(12) United States Patent
Sano et al.

(10) Patent No.: US 8,530,559 B2
(45) Date of Patent: Sep. 10, 2013

(54) COMPOSITE OF ORGANIC COMPOUND AND COPPER NANOPARTICLES, COMPOSITE OF ORGANIC COMPOUND AND COPPER(I) OXIDE NANOPARTICLES, AND METHODS FOR PRODUCING THE COMPOSITES

(75) Inventors: Yoshiyuki Sano, Sakura (JP); Ren-Hua Jin, Sakura (JP); Kaori Kawamura, Sakura (JP); Masafumi Uota, Sakura (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 13/634,344

(22) PCT Filed: Feb. 28, 2011

(86) PCT No.: PCT/JP2011/054454
§ 371 (c)(1),
(2), (4) Date: Dec. 20, 2012

(87) PCT Pub. No.: WO2011/118339
PCT Pub. Date: Sep. 29, 2011

(65) Prior Publication Data
US 2013/0095320 A1 Apr. 18, 2013

(30) Foreign Application Priority Data
Mar. 24, 2010 (JP) .................................. 2010-067853

(51) Int. Cl.
*C08K 3/10* (2006.01)
(52) U.S. Cl.
USPC ........... 524/403; 428/402; 556/113; 556/117; 977/773; 977/896
(58) Field of Classification Search
USPC ....................................... 524/403
See application file for complete search history.

(56) References Cited

U.S. PATENT DOCUMENTS

| 2007/0051927 A1 | 3/2007 | Itoh et al. | |
| 2008/0157029 A1* | 7/2008 | Lee et al. | 252/512 |
| 2009/0226711 A1* | 9/2009 | Silvi et al. | 428/331 |

FOREIGN PATENT DOCUMENTS

| JP | 2004-119686 A | 4/2004 |
| JP | 2004-143571 A | 5/2004 |
| JP | 2004-190089 A | 7/2004 |
| JP | 2009-259804 A | 11/2009 |

(Continued)

OTHER PUBLICATIONS

International Search Report for PCT/JP2011/054454, mailing date of Apr. 5, 2011.

(Continued)

Primary Examiner — Doris Lee
(74) Attorney, Agent, or Firm — Westerman, Hattori, Daniels & Adrian, LLP

(57) ABSTRACT

Provided is a composite including copper nanoparticles or copper(I) oxide nanoparticles and a thioether-containing organic compound represented by $X(OCH_2CHR^1)_n OCH_2CH(OH)CH_2SZ$ [X represents an alkyl group; $R^1$ represents a hydrogen atom or a methyl group; n represents an integer of 2 to 100; $R^1$ is independent between repeating units and may be the same or different; and Z represents an alkyl group, an allyl group, an aryl group, an arylalkyl group, $-R^2-OH$, $-R^2-NHR^3$, or $-R^2-(COR^4)_m$ (where $R^2$ represents a saturated hydrocarbon group; $R^3$ represents a hydrogen atom, an acyl group, an alkoxycarbonyl group, or a benzyloxycarbonyl group; $R^4$ represents a hydroxy group, an alkyl group, or an alkoxy group; and m represents 1 to 3)]. Provided is a method for producing a composite of an organic compound and copper nanoparticles or a composite of an organic compound and copper(I) oxide nanoparticles, the method including reducing a copper compound in the presence of a thioether-containing organic compound represented by the general formula (1) above.

14 Claims, 5 Drawing Sheets

(56) References Cited

FOREIGN PATENT DOCUMENTS

WO 2005/037465 A1 4/2005

OTHER PUBLICATIONS

J. H. Clark, "Fluoride Ion as a Base in Organic Synthesis", Chem. Re. vol. 80, pp. 429-452, Department of Chemistry, University of York, (1980).

S. J. Jungk et al, "Efficient Synthesis of C-Pivot Lariat Ethers. 2-(Alkoxymethyl)-1,4,7,10,13,16-hexaoxacycloocta-decanes[1]", J. Org. Chem. vol. 48, pp. 1116-1120, Department of Chemistry, Louisiana State University, (1983).

D. Albanese et al, "Tetrabutylammonium Fluoride: A Powerful Catalyst for the Regioselective Opening of Epoxides with Thiols", Short Papers, Synthesis, Dipartimento di Chimica, pp. 34-36, (1993).

\* cited by examiner 50 nm 50 nm

COMPOSITE OF ORGANIC COMPOUND AND COPPER NANOPARTICLES, COMPOSITE OF ORGANIC COMPOUND AND COPPER(I) OXIDE NANOPARTICLES, AND METHODS FOR PRODUCING THE COMPOSITES

TECHNICAL FIELD

The present invention relates to a composite of a thioether-containing organic compound having a specific structure and copper nanoparticles or copper(I) oxide nanoparticles. The present invention also relates to methods for producing a composite of an organic compound and copper nanoparticles and a composite of an organic compound and copper(I) oxide nanoparticles, in which a thioether-containing organic compound is used as a copper-colloid protective agent and a copper compound is reduced in the presence of the copper-colloid protective agent.

BACKGROUND ART

In recent years, the facts that fine metal particles having a particle size on the nanometer level (hereafter referred to as metal nanoparticles) exhibit physical properties different from those of normal bulk metals have been continuously revealed. Novel materials employing such properties are being intensively developed. In particular, attempts to use metal nanoparticles as conductive printing materials employing the phenomenon that metal nanoparticles have a fusion temperature much lower than that of bulk metal have been widely made. For example, although silver normally has a melting point of more than 960° C., a phenomenon has been observed that nanoparticles thereof having a size of 100 nm or less readily fuse together even at a low temperature of about 200° C. Accordingly, when an ink containing metal nanoparticles exhibiting low-temperature fusibility is prepared, good electrical wiring can be formed by only drawing a circuit by a printing process and then sintering the circuit at a low temperature. This novel circuit-formation method is markedly simple and economical, compared with photolithography in which physical and chemical treatments such as masking and etching treatments are repeatedly performed.

Under such circumstances, practical use of gold nanoparticles and silver nanoparticles as conductive materials has evolved. In addition, nanoparticles of noble metals such as palladium, rhodium, and platinum that are excellent in catalysis are being used in wider applications. Compared with such nanoparticles, copper nanoparticles may be produced at low cost because copper compounds serving as raw materials are inexpensive. However, compared with other noble metals, as for copper, it is difficult to control particle size on the nanometer level or to ensure dispersion stability. In addition, copper is very susceptible to oxidation. Accordingly, the development of copper nanoparticles has not sufficiently advanced.

On the other hand, there is a method in which partial oxidation of copper is regarded as being unavoidable and oxidized copper is reduced during sintering. Specifically, various physical techniques have been developed: for example, a technique in which a dispersion liquid of copper nanoparticles is applied to a substrate to form a thin film or to draw a conductive pattern, and a wiring pattern is then completed under a reducing atmosphere such as hydrogen gas, ammonia, carbon monoxide, atomic hydrogen, or alcohol vapor; and a technique in which metal nanoparticles are fused together by high-frequency irradiation to form a porous conductive thin film. Together with developments of apparatuses such as a microwave hydrogen-plasma generator and a pulse photon emitting apparatus, various techniques have been provided for the purpose of achieving practical use of a dispersion of copper nanoparticles. A stable dispersion of copper nanoparticles has been demanded.

Fine copper particles have been synthesized since a long time ago by a method (polyol reduction method) in which a copper salt, a copper oxide, or the like is treated at a high temperature in a polyhydric alcohol having a high boiling point. However, this method tends to provide relatively large particles having a size of several hundred nanometers to about one micrometer and the particles do not have the low-temperature sinterability that is expected for electronic materials.

Afterwards, synthesis of reduced metal nanoparticles having a size of 100 nm or less was achieved by adding, to the reaction system, a polymer substance such as polyvinyl pyrrolidone or an amine-based organic compound. Thus, the phenomenon that fusion occurs at a low temperature of 300° C. or less can be expected, and application of the particles to an efficient printing technique, an inkjet process, has come to be realized. Such polyvinyl pyrrolidone and an amine-based compound are compounds having a function of adhering to generated metal nanoparticles to suppress an increase in the particle size and a function of stably maintaining and dispersing generated metal nanoparticles in a medium. These compounds are referred to as capping agents and colloid protective agents. These are indispensable for formation of metal nanoparticles and also serve as factors dictating characteristics such as fusion temperature, and thus are the important technical component for practical use of metal nanoparticles.

Such a metal-colloid protective agent needs a structure that is compatible with a solvent and imparts a dispersion stabilization function through exhibition of repulsion in response to the close presence of metal nanoparticles, and a partial structure that has an affinity allowing adsorption of the structure onto the metal nanoparticles. These structures may be the same structure or different chemical structures. In consideration of dispersion in an aqueous medium, the former structure may be a hydrophilic polymer structure such as polyethylene glycol, a copolymer between polyethylene glycol and polypropylene glycol, polyethyleneimine, polyacrylamide, polyvinyl acetate, polyvinyl alcohol, or polyvinyl pyrrolidone. When the medium is an organic solvent, a hydrophobic functional group such as a long-chain alkyl group or a phenyl group is used.

On the other hand, the affinity for metal surfaces is provided by a hetero functional group. Specifically, a lone electron-pair in a hetero atom is coordinated to a metal ion or the surface of a metal nanoparticle to thereby achieve the adsorption. Examples of commonly used adsorptive functional groups include —OH, —O—, —SH, —CN, —NH$_2$, —NR$_3$, —SO$_2$OH, —SOOH, —OPO(OH)$_2$, and —COOH. In particular, compounds having a —SH group or a —COOH group have a very high affinity for copper and copper compounds and are used in many cases (for example, refer to Patent Literature 1).

In general, coordination of the thiol functional group (—SH) to the surface of a metal nanoparticle has a very high strength that is similar to a covalent bond. Accordingly, when a thiol compound is used as a protective agent, the protective agent having coordinated is not easily dissociated. For this reason, in general, the protective agent is dissociated by heating to the decomposition temperature of the thiol functional group. Thus, use of nano metal as a conductive material in which a thiol compound is used as the protective agent exerts large detrimental effects. On the other hand, it is known that the thioether (C—S—C) functional group can coordinate to metal, but this coordination has a weak strength; and the group is considered to have a high affinity for copper nanoparticles (for example, refer to Patent Literature 2). However, there have been no cases where the group is actually incorporated as an affinity functional group into a colloid protective agent and used for producing copper nanoparticles or copper(I) oxide nanoparticles.

Citation List

Patent Literature

PTL 1: Japanese Unexamined Patent Application Publication No. 2004-143571

PTL 2: Japanese Unexamined Patent Application Publication No. 2004-119686

SUMMARY OF INVENTION

Technical Problem

Under the above-described circumstances, an object of the present invention is to provide a composite containing an organic compound that is useful as a protective agent allowing stable dispersion of copper nanoparticles or copper(I) oxide nanoparticles in a medium, and such particles; and to provide a simple method for producing the composite.

Solution to Problem

Metal nanoparticles that are useful as a conductive material can be stably dispersed in a medium for a long period of time; when the dispersion liquid is applied to a substrate and dried, in the resultant thin film, the metal nanoparticles easily fuse together; and adhesion between the thin film and the substrate is sufficiently achieved. To impart such properties to copper nanoparticles or copper(I) oxide nanoparticles, a protective agent needs to be designed that has a functional group having a high capability of allowing stable dispersion and has an appropriate affinity for the surfaces of copper particles or copper(I) oxide particles.

The inventors of the present invention performed thorough studies. As a result, the inventors have found that a reaction between a copper compound and a reducing agent in the presence of an organic compound having a specific structure including a thioether group (sulfide bond) provides a composite in which copper nanoparticles are protected by the organic compound and a composite in which copper(I) oxide nanoparticles are protected by the organic compound, and such a composite state allows stable dispersion in a medium for a long period of time. In addition, the inventors have found that, when a dispersion liquid of a composite of the organic compound and copper nanoparticles is applied to form a coating film in the air or an inert gas, the polymer is easily dissociated from the composite and fusion among copper nanoparticles proceeds to thereby provide a thin film having a metallic luster; and the thin film is subjected to a heat treatment at a relatively low temperature in a reducing atmosphere to thereby form a film having a high conductivity. Thus, the present invention has been accomplished.

Specifically, the present invention provides a composite of an organic compound and copper nanoparticles or a composite of an organic compound and copper(I) oxide nanoparticles, the composite including a thioether-containing organic compound (A) represented by a general formula (1) below and copper nanoparticles (B) or copper(I) oxide nanoparticles (C)

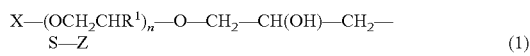
(1)

[in the formula (1), X represents a $C_1$ to $C_8$ alkyl group; $R^1$ represents a hydrogen atom or a methyl group; n represents a repeating number, an integer of 2 to 100; $R^1$ is independent between repeating units and may be the same or different; and Z represents a $C_2$ to $C_{12}$ alkyl group, an allyl group, an aryl group, an arylalkyl group, —$R^2$—OH, —$R^2$—$NHR^3$, or —$R^2$—$(COR^4)_m$ (where $R^2$ represents a $C_1$ to $C_4$ saturated hydrocarbon group; $R^3$ represents a hydrogen atom, a $C_2$ to $C_4$ acyl group, a $C_2$ to $C_4$ alkoxycarbonyl group, or a benzyloxycarbonyl group that may optionally have, as a substituent on the aromatic ring, a $C_1$ to $C_4$ alkyl group or a $C_1$ to $C_8$ alkoxy group; $R^4$ represents a hydroxy group, a $C_1$ to $C_4$ alkyl group, or a $C_1$ to $C_8$ alkoxy group; and m represents 1 to 3)].

The present invention also provides a method for producing a composite of an organic compound and copper nanoparticles or a composite of an organic compound and copper(I) oxide nanoparticles, the method including reducing a copper compound in the presence of the thioether-containing organic compound (A) represented by the general formula (1) above.

ADVANTAGEOUS EFFECTS OF INVENTION

A dispersion liquid of a composite of an organic compound and copper nanoparticles and a dispersion liquid of a composite of an organic compound and copper(I) oxide nanoparticles according to the present invention are dispersion liquids in which stable dispersion can be ensured for 1 to 3 or more months under hermetic storage at room temperature. The copper nanoparticles and the copper(I) oxide nanoparticles are controlled to have a particle size of 2 to 80 nm; for example, by heating at 180° C. for 2 hours in a reducing atmosphere (such as a hydrogen atmosphere), a copper film having a volume resistivity of about $10^{-5}$ to about $10^{-6}$ Ωcm can be easily produced. Accordingly, a dispersion liquid of a composite of an organic compound and copper nanoparticles and a dispersion liquid of a composite of an organic compound and copper(I) oxide nanoparticles according to the present invention can provide conductive inks used for, for example, formation of a circuit pattern, conductive bonding agents, and thermal conductors. The dispersion liquid of a composite containing copper(I) oxide nanoparticles can be used to form a semiconductor film having photoresponsivity.

DESCRIPTION OF EMBODIMENTS

Figure 1:
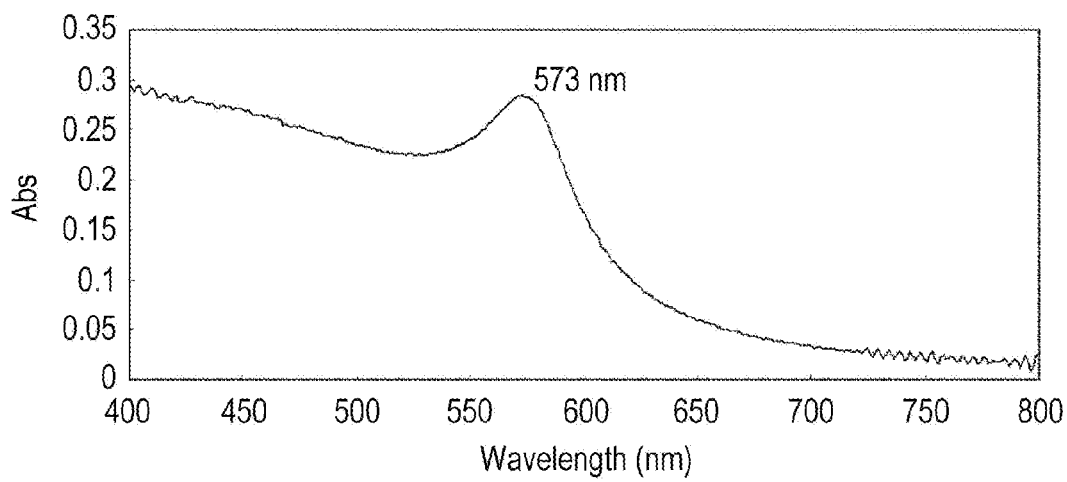
FIG. 1 illustrates an ultraviolet-visible absorption spectrum of a dispersion liquid of a composite of an organic compound and copper nanoparticles in EXAMPLE 1.

Hereinafter, the present invention will be described in detail.

[Thioether-Containing Organic Compound (A)]

As described above, to achieve dispersion stability, low-temperature sinterability, and adhesion that are desired in copper nanoparticles or copper(I) oxide nanoparticles that are useful as a conductive material, it is important to design a protective agent having an appropriate affinity adsorptivity to the surfaces of copper or copper(I) oxide particles. As for sulfur-containing groups serving as affinity groups for metal surfaces, the most commonly used are thiols (R—SH). These form thiolate bonds such as R—S— Metal to exhibit a very high affinity for metal surfaces. When such compounds that form persistent bonds are used as protective agents for metal nanoparticles, dissociation of the protective agents from the surfaces of metal particles is inhibited and, as a result, the low-temperature fusion phenomenon is less likely to be achieved. In addition, thiols tend to be easily oxidized to form a disulfide and do not have sufficient storability as compounds. Accordingly, the sulfur-containing group is preferably of a thioether type (R—S—R') in terms of balance between affinity for and dissociability from the surfaces of metal particles, and compound stability.

In the present invention, as a functional group contributing to dispersion stability in a protective agent for copper nanoparticles or copper(I) oxide nanoparticles, a linear functional group having ethylene glycol or propylene glycol as the repeating unit is selected. The number of the unit repeated is generally 2 to 100, in particular, preferably 20 to 50 because higher dispersion stability is achieved.

The linear functional group having ethylene glycol or propylene glycol as the repeating unit needs to have a nonreactive group at an end and, at another end, a reactive group for introducing the above-described thioether structure. The nonreactive group is, in view of the production method, ease of industrial availability, and dispersion stability in the use as a protective agent, a linear or branched alkyl group having 1 to 8 carbons; in particular, preferably an alkyl group having 1 to 4 carbons in view of stability in an aqueous medium.

As the reactive group at the other end, epoxide is selected because the thioether structure can be easily introduced by a process described below. A structure having epoxide can be coupled with a thiol compound irrespective of position and the presence or absence of modification. However, the reactive group at the end is preferably a glycidyl group because epichlorohydrin, which is readily available, can be used as a raw material and is introduced by a simple method. In this case, the resultant thioether-containing organic compound (A) has a 2-hydroxysulfide structure introduced and serving as a bidentate ligand and it has higher affinity for copper nanoparticles or copper(I) oxide nanoparticles.

As a result of the above-described considerations, the inventors of the present invention have selected, as a protective agent, a polymer having a structure represented by a general formula (1) below.

$$X-(OCH_2CHR^1)_n-O-CH_2-CH(OH)-CH_2-S-Z \quad (1)$$

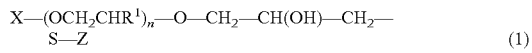

[in the formula (1), X represents a $C_1$ to $C_8$ alkyl group; $R^1$ represents a hydrogen atom or a methyl group; n represents a repeating number, an integer of 2 to 100; $R^1$ is independent between repeating units and may be the same or different; and Z represents a $C_2$ to $C_{12}$ alkyl group, an allyl group, an aryl group, an arylalkyl group, —$R^2$—OH, —$R^2$—$NHR^3$, or —$R^2$—$(COR^4)_m$ (where $R^2$ represents a $C_1$ to $C_4$ saturated hydrocarbon group; $R^3$ represents a hydrogen atom, a $C_2$ to $C_4$ acyl group, a $C_2$ to $C_4$ alkoxycarbonyl group, or a benzyloxycarbonyl group that may optionally have, as a substituent on the aromatic ring, a $C_1$ to $C_4$ alkyl group or a $C_1$ to $C_8$ alkoxy group; $R^4$ represents a hydroxy group, a $C_1$ to $C_4$ alkyl group, or a $C_2$ to $C_8$ alkoxy group; and m represents 1 to 3)].

Of these, compounds having a short chain in which the number n of the repeating unit is 1 or 2 and having Z that is a simple alkyl group or 2-hydroxyethyl (—$CH_2CH_2OH$) group are known compounds. However, compounds that have a polymerization degree (n=about 10 to about 45) corresponding to a molecular weight of 500 to 2000 and have excellent functions as a protective agent for metal nanoparticles are not known. Furthermore, compounds having a structure in which Z contains a carboxyl group, an alkoxycarbonyl group, a carbonyl group, an amino group, or an amido group as a partial structure can constitute, with a hydroxy group derived from epoxide or a thioether group, polydentate ligands, have a very high affinity for the surfaces of metal particles, and are optimal as protective agents for copper nanoparticles/copper(I) oxide nanoparticles.

[Method for Producing Thioether-Containing Organic Compound (A)]

As described above, a protective agent used in the present invention is a compound represented by the general formula (1). Hereinafter, a method for synthesizing the organic compound (A) will be described in detail.

A method for simply synthesizing the thioether-containing organic compound (A) may be a method in which a polyether compound (a1) having a glycidyl group at an end is caused to react with a thiol compound (a2).

The polyether compound (a1) having a glycidyl group at an end can be represented by a general formula (2) below.

[Chem. 1]

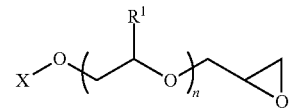

(2)

(In the formula, X, $R^1$, and n are the same as above.)

A method for synthesizing the polyether compound (a1) having a glycidyl group at an end may be, for example, a method in which a polyethylene/polypropylene glycol monoalkyl ether is added to the oxirane ring of epichlorohydrin in the presence of a Lewis acid to open the ring and the generated chlorohydrin compound is then heated in an alkali at a high concentration to close the ring; or a method in which the reaction is conducted by a single step employing an excess alcoholate or a strong base such as a high-concentration alkali. To obtain a polyether compound (a1) having a higher purity, a method by Gandour et al. (Gandour, et al., J. Org. Chem., 1983, 48, 1116.) in which polyethylene/polypropylene glycol monomethyl ether is turned into an alkoxide with potassium t-butoxide, condensation between the alkoxide and epichlorohydrin is caused, and the heating is then continued to form the epoxy ring again is preferably appropriately applied.

The target thioether-containing organic compound (A) can be obtained by opening, with the thiol compound (a2), the end oxirane ring of the polyether compound (a1) having a glycidyl group at an end. Although this reaction employs a nucleophilic reaction of a thiol group, the reaction may be achieved by various activation processes.

For example, synthesis by activation of epoxide using a Lewis acid is commonly conducted. Specifically, use of zinc tartrate and lanthanide Lewis acids is known. In addition, a process using a Lewis base is often conducted.

A process employing fluorine ions as a basic catalyst is described in detail in the review article by James H. Clark. Penso et al. applied this process as an epoxide ring-opening process excellent in regioselectivity and reported that, by using quaternary ammonium fluoride as a catalyst, a ring-opening reaction by addition of thiol to epoxide proceeds under mild conditions.

In particular, to efficiently obtain the thioether-containing organic compound (A) used in the present invention, the process employing fluorine ions as a basic catalyst is preferably used. By applying this process, the thioether-containing organic compound (A) usable in the present invention can be obtained without special purification after the reaction between the polyether compound (a1) having a glycidyl group at an end and the thiol compound (a2).

The polyether compound (a1) can be caused to react with various thiol compounds (a2): for example, alkanethiols; benzenethiols; and commonly used radical-polymerization chain transfer agents, which are readily available, including thioglycol, thioglycolic acid and esters thereof, mercaptopropionic acid and esters thereof. The reaction may be performed with mercaptopolycarboxylic acids such as thiomalic acid, thiocitric acid, and esters of the foregoing. Similarly, the reaction may be performed with compounds intramolecularly having a plurality of thiol groups to introduce the compounds; examples of the compounds include alkylenedithiols such as ethanedithiol, trimethylolpropane=tris(3-mercaptopropionate), pentaerythritol=tetrakis(3-mercaptopropionate), and dipentaerythritol=hexakis(3-mercaptopropionate). The resultant compounds intramolecularly have a plurality of thioether structures and hence the plurality of regions can exhibit affinity for copper nanoparticles and copper(I) oxide nanoparticles.

[Composite of Organic Compound and Copper Nanoparticles]

A composite of an organic compound and copper nanoparticles according to the present invention contains the above-described thioether-containing organic compound (A) and copper nanoparticles (B) having a particle size on the nanometer order. In particular, copper nanoparticles having an average particle size of 2 to 50 nm are covered with the thioether-containing organic compound (A) to form a particulate composite on the whole.

The particle size and particle-size distribution of the copper nanoparticles (B) can be measured with a transmission electron microscope image (hereafter referred to as TEM). The shape of the composite of an organic compound and copper nanoparticles can also be observed with TEM. The particle size and particle-size distribution of the particulate composite can be measured by dynamic light scattering in combination with TEM observation.

The average particle size (primary particle size) of 100 particles of the composite in a TEM image is preferably in the range of 2 to 80 nm in the case of using the composite as a conductive material or the like. The average particle size determined by dynamic light scattering is larger than the particle size determined by TEM observation and it is about 30 to about 110 nm.

An aqueous dispersion of the composite of an organic compound and copper nanoparticles having been purified as described below is dried and solidified to provide nonvolatile matter. The weight loss percentage of the nonvolatile matter through ignition is determined with a thermogravimetric analyzer (TG/DTA method). The weight loss percentage can be regarded as the content of the organic compound in the composite. The content of the thioether-containing organic compound (A) determined in this manner is preferably 2% to 8% by mass in the case of using the composite or the dispersion thereof as a conductive material or the like.

Wide-angle X-ray diffractometry has demonstrated that metal particles constituting the composite are composed of zero-valent reduced copper only. The content of copper(0) can be regarded as being obtained by subtracting the content of the organic compound determined by the TG/DTA method from the weight of nonvolatile matter.

[Composite of Organic Compound and Copper(I) Oxide Nanoparticles]

A composite of an organic compound and copper(I) oxide nanoparticles according to the present invention contains the above-described thioether-containing organic compound (A) and copper(I) oxide nanoparticles (C) having a particle size on the nanometer order. In particular, copper(I) oxide nanoparticles having an average particle size of 2 to 50 nm are covered with the thioether-containing organic compound (A) to form a particulate composite on the whole. As to the composite of an organic compound and copper(I) oxide nanoparticles, the particle size and the content of copper(I) oxide can be determined as in the composite of an organic compound and copper nanoparticles. The primary particle size of the composite of an organic compound and copper(I) oxide nanoparticles in a TEM image is preferably in the range of 2 to 80 nm in view of applications. The average particle size determined by dynamic light scattering is larger than the particle size determined by TEM observation and it is about 30 to about 110 nm. The content of the thioether-containing organic compound (A) in the composite is preferably 2% to 8% by mass in the case of using the composite as a material in various application processes.

[Methods for Producing Composite of Organic Compound and Copper Nanoparticles and Composite of Organic Compound and Copper(I) Oxide Nanoparticles]

Methods for producing a composite of an organic compound and copper nanoparticles and a composite of an organic compound and copper(I) oxide nanoparticles according to the present invention include, in the presence of the above-described thioether-containing organic compound (A), a step of mixing a divalent copper-ion compound with a solvent and a step of reducing the copper ions.

The divalent copper-ion compound may be normally available copper compounds and examples thereof include sulfate, nitrate, carboxylate, carbonate, chloride, and acetylacetonato complex. In the case of obtaining the composite containing the zero-valent copper nanoparticles (B), the starting compound may be divalent or monovalent and may contain water or crystal water. In the case of producing the composite containing the copper(I) oxide nanoparticles (C), a divalent copper compound may be partially reduced. Specific examples include, without description of crystal water, $CuSO_4$, $Cu(NO_3)_2$, $Cu(OAc)_2$, $Cu(CH_3CH_2COO)_2$, $Cu(HCOO)_2$, $CUCO_3$, $CUCl_2$, $CU_2O$, and $C_5H_7CuO_2$. In addition, basic salts obtained by subjecting the above-described salts to heating or exposure to a basic atmosphere, such as $Cu(OAc)_2 \cdot CuO$, $Cu(OAc)_2 \cdot 2CuO$, and $Cu_2Cl(OH)_3$, are most preferably used. These basic salts may be prepared within the reaction system or may be separately prepared outside the reaction system and used. An ordinary process in which ammonia or an amine compound is added to form a complex to ensure solubility and the complex is then used for reduction may be employed.

Such a copper-ion compound is dissolved in or mixed with a medium in which the thioether-containing organic compound (A) has been dissolved or dispersed in advance. The medium usable at this time depends on the structure of the organic compound (A) used. When the composite is produced with a polyethylene glycol-based organic compound (A), preferred media include water, ethanol, acetone, ethylene glycol, diethylene glycol, glycerin, and mixtures of the foregoing; in particular, the mixture of water and ethylene glycol is preferred. On the other hand, when a polypropylene glycol-based organic compound (A) is used, usable media include glyme-based solvents such as ethylene glycol dimethyl ether, diethylene glycol dimethyl ether, propylene glycol methyl ether acetate, and butyl diethylene glycol acetate.

The concentration of the thioether-containing organic compound (A) in various media is preferably adjusted to satisfy the range of 0.3% to 10% by mass because the subsequent reduction reaction can be easily controlled.

To the medium prepared above, the divalent copper-ion compound is added all at once or in portions and mixed. When a medium having low solubility for the compound is used, the compound may be dissolved in a small amount of a good solvent and then added to the medium.

The mixing proportion of the thioether-containing organic compound (A) and the copper-ion compound is preferably appropriately selected in accordance with the protection capability of the thioether-containing organic compound (A) in the reaction medium. In general, with respect to 1 mol of the copper-ion compound, the thioether-containing organic compound (A) is preferably used in the range of 1 mmol to 30 mmol (about 2 to about 60 g in the case of using a polymer having a molecular weight of 2000), in particular, in the range of 15 to 30 mmol.

The copper ions are then reduced with various reducing agents. The reducing agents are preferably compounds that can cause the reduction reaction of copper at ice-cold temperature to 80° C. or less such as hydrazine compounds, hydroxylamine and derivatives thereof, metal hydrides, phosphinates, aldehydes, enediols, and hydroxyketones because a composite in which copper mirror or precipitate is less likely to be formed is provided.

Specifically, strong reducing agents may be used such as hydrazine hydrates, uns-dimethylhydrazine, an aqueous solution of hydroxylamine, and sodium borohydride. These agents have the capability of reducing copper compounds to zero valence and hence are suitable for the cases where divalent and monovalent copper compounds are turned into reduced copper to produce composites of an organic compound and copper nanoparticles. To obtain the copper(I) oxide nanoparticles (C), a hydrazine hydrate, uns-dimethylhydrazine, or an aqueous solution of hydroxylamine is slowly added such that the addition equivalent is suppressed to about quarter in mol or partial reduction is performed with ascorbic acid, acetaldehyde, hydroxyacetone, N,N-diethylhydroxylamine, or the like. These reducing agents may be used alone or in combination.

Conditions suitable for reduction reactions vary in accordance with copper compounds used as starting materials, the type of reducing agents, whether complexation is performed or not, media, and the type of the thioether-containing organic compound (A). For example, when copper(II) acetate is reduced with sodium borohydride in an aqueous system, the zero-valent copper nanoparticles (B) can be prepared even at about ice-cold temperature. In contrast, when hydrazine is used, the reaction slowly proceeds at room temperature and heating to about 60° C. allows smooth reduction reaction. When complexation is performed with ammonia, the oxidation-reduction potential of complex ions becomes more noble and hence a higher temperature by about 20° C. is required. In determination of reaction conditions, monitoring of the reaction is indispensable. Change in the color of the reaction system is important information. The completion of the reaction is indicated by disappearance of the color of ammine copper ions generated by addition of high-concentration aqueous ammonia to the reaction solution or the filtrate of the reaction solution through ultrafiltration. Use of copper-ion test strips (Merckoquant 1.10003 from Merck) indicates semi-quantitative reaction percentage. The reduction reaction is performed under such monitoring until the reaction is completed. Reduction of copper acetate in an ethylene glycol/aqueous system at 60° C. requires reaction time of about 2 hours. When the reduction reaction is thus completed, a reaction mixture containing a composite of an organic compound and copper nanoparticles or a composite of an organic compound and copper(I) oxide nanoparticles is obtained.

[Method for Producing Dispersion Liquid]

After the reduction reaction, a step of removing the copper compound residue, the reducing reagent residue, the excess thioether-containing organic compound (A), and the like is optionally performed. In particular, when the amount of the excess thioether-containing organic compound (A) is large, fusion between the copper nanoparticles (B) or the copper(I) oxide nanoparticles (C) contained in such a composite may be inhibited. Accordingly, when the composite is used as a conductive material, a purification step of removing such substances is indispensable. To purify the composite, reprecipitation, centrifugal sedimentation, or ultrafiltration may be applied; the resultant reaction mixture containing the composite is washed with a washing solvent such as water, ethanol, acetone, or a mixture of the foregoing to thereby wash away the above-described impurities.

In a final stage of the purification, instead of adding the washing solvent to the composite, a solvent corresponding to an intended use may be added to the composite to exchange the media, so that a dispersion in which the composite is dispersed in the solvent selected in accordance with the intention can be prepared. For example, by adding water, ethanol, or a mixture of the foregoing, a dispersion that can be easily dried is provided, which is suitable as a conductive material.

Alternatively, after the substitution with water or ethanol is performed, a solvent that has a higher boiling point than water or ethanol such as toluene, diethylene glycol dimethyl ether, or propylene glycol methyl ether acetate may be added and water or ethanol may be subsequently evaporated to provide a nonpolar-solvent dispersion. In this case, the dispersion can be applied to, for example, an inkjet printing process.

The concentration of the dispersion can be adjusted to various values in accordance with intended uses. Since required concentrations are about 5% to about 40% by mass in general coating applications and about 20% to about 80% by mass in inkjet printing applications, the amount of the medium added may be appropriately adjusted to achieve such a concentration. When the thus-prepared dispersion of a composite is stored in a sealed vessel, it is stable for about 1 to about 3 months irrespective of the concentration adjusted.

[Methods for Producing Copper Film and Copper Oxide Film]

By simply applying the obtained dispersion of a composite to a substrate with a bar coater or the like and drying the dispersion in an inert gas, a thin film having a metallic luster can be obtained. Even when the drying is performed in the air, a metallic luster film is similarly obtained. The film is placed in a sealed vessel; the atmosphere is substituted with hydrogen and the film is heated at 180° C. for 2 hours; the resistivity and film thickness of the thin film are then measured to evaluate the conductivity of the thin film. Thus, the function of the conductive material can be evaluated.

The substrate is not particularly limited as long as it can withstand the sintering temperature; glass and polyimide films can be used in this application. Examples of the atmosphere include, in addition to hydrogen, carbon monoxide, vapor of an alcohol such as ethylene glycol or glycerin, mixtures of the foregoing, and a reducing gas diluted with an inert gas such as nitrogen or argon. When alcohol vapor is used, heating at about 250° C. to about 300° C. is required; accordingly, hydrogen and carbon monoxide are preferred in view of low heating temperature.

EXAMPLES

Hereinafter, the present invention will be described with reference to examples. "Parts" and "%" are based on mass unless otherwise specified.

$^1$H-NMR Measurement

A compound (about 20 mg) to be measured was dissolved in about 0.8 mL of 0.03% tetramethylsilane-containing deuterochloroform, charged into a glass sample tube (outer diameter: 5 mm) for NMR measurement, and measured with a JEOL JNM-LA300 nuclear magnetic resonance absorption spectrum measurement apparatus to obtain a $^1$H-NMR spectrum. The chemical shift value δ was indicated with tetramethylsilane serving as a reference material.

Measurement of Ultraviolet-Visible Absorption Spectrum

A single droplet of a dispersion of a composite was added to about 10 mL of ethylene glycol and shaken. The resultant solution was immediately measured in terms of the ultraviolet-visible absorption spectrum with an MV-2000 photodiode-array ultraviolet-visible absorption spectrum measurement apparatus manufactured by JASCO Corporation with sweeping from 400 nm to 800 nm for 0.1 seconds.

Measurement of Electric Resistivity of Copper Thin Film

The film obtained above was measured in terms of surface resistivity (Ω/square) with a Loresta GP MCP-T610 low resistivity meter (manufactured by Mitsubishi Chemical Corporation) in compliance with JIS K7194 "Tests for resistivity of conductive plastics with a four-point probe array". From the thickness (cm) of the thin film and the surface resistivity (Ω/square), volume resistivity (Ωcm) was calculated with the following equation.

Volume resistivity(Ωcm)=Surface resistivity
(Ω/square)×Thickness(cm)

The thickness of the film was measured with a 1LM15 scanning laser microscope (manufactured by Lasertec Corporation).

Measurement of Particle Size and Particle-Size Distribution

TEM Observation

A small amount of a dispersion was diluted with purified water and a droplet of the dilution was immediately dropped onto a copper grid having a collodion film for electron microscopy. This droplet was microscopically observed with a JEM-2200FS transmission electron microscope (200 kv, manufactured by JEOL Ltd.). From the resultant micrographic image, the particle size was determined.

Measurement of Particle-Size Distribution by Dynamic Light Scattering

A portion of a dispersion was diluted with ethylene glycol and measured in terms of particle-size distribution and average particle size with a FPAR-1000 high-concentration particle-size analyzer (Otsuka Electronics Co., Ltd.). At this time, the measurement was performed at 25° C. and the analysis was performed with the proviso that the medium had a refractive index of 1.4306 and a viscosity of 17.4 cP.

Wide-Angle X-ray Diffractometry

Dispersion: A dispersion was charged into a liquid sample holder and immediately measured in terms of the intensity of diffracted X-ray with respect to diffraction angle (2θ) with a RINT TTR2 (50 kv, 300 mA, manufactured by Rigaku Corporation).

Copper film: A slide glass having a copper film was cut into an appropriate size, placed on a specimen platform, and immediately measured and recorded in terms of the intensity of diffracted X-ray with respect to diffraction angle (2θ) with a RINT TTR2 (50 kv, 300 mA, manufactured by Rigaku Corporation).

Content of Copper/Copper(I) Oxide by Thermal Analysis (Thermogravimetric Analysis (TG/DTA Method)

About 1 mL of the obtained dispersion was sampled in a glass sample vial and heated to be concentrated on hot water under nitrogen flow. The residue was vacuum-dried at 40° C. for 8 hours to provide dry solid matter. About 5 mg of the dry solid matter was accurately weighed to an aluminum pan for thermogravimetric analysis, placed on an EXSTAR TG/DTA 6300 differential thermogravimetric analyzer (manufactured by Seiko Instruments Inc.), and heated at a rate of 10° C./min from room temperature to 500° C. under nitrogen flow to measure weight loss percentage in heating. The content of copper or copper(I) oxide was calculated with the following equation.

Content(%)=100−Weight loss percentage(%)

Synthesis Example 1

Polyethylene Glycol Methyl Glycidyl Ether
(Molecular Weight of Polyethylene Glycol Chain: 2000)

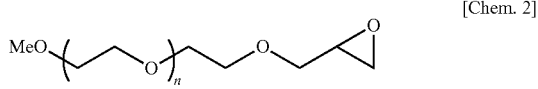

[Chem. 2]

To 1000 g of dehydrated toluene, potassium t-butoxide (100.8 g, 0.8983 mol) was added and stirred. To this mixture, a toluene (2000 g) solution of a polyethylene glycol monomethyl ether (molecular weight: 2000, 600 g) was added dropwise over 3 hours at room temperature. In this state, the mixture was stirred for 2 hours at room temperature, then heated to 40° C., and further stirred for 2 hours. To this mixture, epichlorohydrin (168 g, 1.82 mol) was added dropwise at the same temperature, and stirred at 40° C. for 5.5 hours. The reaction mixture was filtered. The filtrate was concentrated. To the resultant residue, chloroform was added to dissolve the residue. This solution was washed with water five times. To the chloroform layer, dry alumina was added to decolorize the layer. The alumina was filtered off and the filtrate was concentrated. The concentration residue was purified by reprecipitation with toluene/n-hexane. The generated solid was collected and dried under a reduced pressure to provide 507.0 g of the target compound (yield: 82%).

¹H-NMR (deuterochloroform): δ=3.9-3.4 (m, polyethylene glycol chain etc.), 3.43 (dd, 1H, J=6.0, 5.7 Hz, one of hydrogens of methylene adjacent to oxirane ring), 3.38 (s, 3H, methoxy group at the terminal of PEG), 3.16 (m, 1H, methine hydrogen of oxirane ring), 2.79 (m, 1H, methylene hydrogen at the terminal of oxirane ring), 2.61 (m, 1H, methylene hydrogen at the terminal of oxirane ring).

Synthesis Example 2

Polyethylene Glycol Methyl Glycidyl Ether
(Molecular Weight of Polyethylene Glycol Chain: 1000)

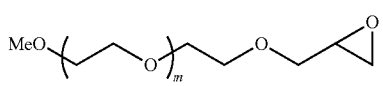

[Chem. 3]

Operations were performed as in Synthesis example 1 except that a polyethylene glycol monomethyl ether (molecular weight: 1000, 305 g) was used instead of the polyethylene glycol monomethyl ether (molecular weight: 2000, 600 g) in Synthesis example 1. As a result, 255.8 g of the target compound was provided (yield: 83%).

¹H-NMR (deuterochloroform): δ=3.9-3.4 (m, polyethylene glycol chain etc.), 3.43 (dd, 1H, J=6.0, 5.7 Hz, one of hydrogens of methylene adjacent to oxirane ring), 3.35 (s, 3H, methoxy group at the terminal of PEG), 3.15 (m, 1H, methine hydrogen of oxirane ring), 2.81 (m, 1H, methylene hydrogen at the terminal of oxirane ring), 2.61 (m, 1H, methylene hydrogen at the terminal of oxirane ring).

Synthesis Example 3

Polypropylene Glycol Butyl Glycidyl Ether
(Molecular Weight of Polypropylene Glycol Chain: 2000)

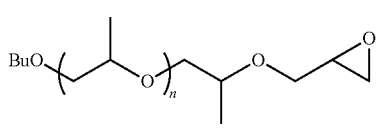

[Chem. 4]

Operations were performed as in Synthesis example 1 except that a polypropylene glycol monobutyl ether (molecular weight: 2000, 600 g) was used instead of the polyethylene glycol monomethyl ether (molecular weight: 2000, 600 g) in Synthesis example 1. As a result, 510.3 g of the target compound was provided (yield: 85%).

¹H-NMR (deuterochloroform): δ=3.7-3.4 (m, polypropylene glycol chain and hydrogens of methylene adjacent to oxygen in butyl group), 3.14 (m, 1H, methine hydrogen of oxirane ring), 2.79 (m, 1H, methylene hydrogen at the terminal of oxirane ring), 2.62 (m, 1H, methylene hydrogen at the terminal of oxirane ring), 1.55 (m, 2H, methylene hydrogens of butyl group), 1.35 (m, 2H, methylene hydrogens of butyl group), 1.15 (md, polypropylene methyl hydrogen), 0.91 (t, 3H, J=7.4 Hz, methyl hydrogens at the terminal of butyl group).

Synthesis Example 4

Thioether-Containing Organic Compound (A-1)

Methyl 3-(3-(methoxy(polyethoxy)ethoxy)-2-hydroxypropylsulfanyl)propionate (addition compound in which methyl 3-mercaptopropionate is added to polyethylene glycol methyl glycidyl ether (molecular weight of polyethylene glycol chain: 2000))

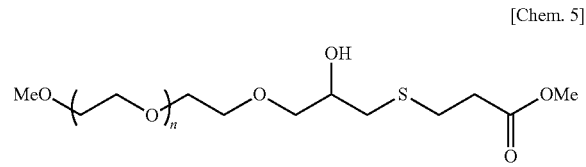

[Chem. 5]

To the polyethylene glycol methyl glycidyl ether (molecular weight of methoxy polyethylene glycol: 2000, 1.00 g) obtained in Synthesis example 1, methyl 3-mercaptopropionate (221 mg, 1.84 mmol) and 1 mol/L tetrabutylammonium fluoride/tetrahydrofuran solution (100 μL, 0.10 mmol) were added, then heated, and stirred at 70° C. to 75° C. for an hour. After the mixture was cooled, to this mixture, 20 mL of water and 20 mL of ethyl acetate were added, sufficiently stirred, and left to stand to achieve phase separation. After that, the aqueous layer was washed with ethyl acetate (20 mL) twice. Addition of sodium sulfate to the aqueous layer resulted in precipitation of oily matter. This oily matter was extracted with methylene chloride (20 mL, three times). The methylene chloride layer was collected, dried over anhydrous sodium sulfate, and then concentrated to dryness to provide 0.94 g of the target thioether-containing organic compound (A-1) (yield: about 89%). ¹H-NMR indicated that extra purification was not necessary for the purity.

¹H-NMR (deuterochloroform): δ=3.9-3.4 (m, polyethylene glycol chain etc.), 3.70 (s, 3H, ester methyl group), 3.38 (s, 3H, methoxy group at the terminal of PEG), 2.84 (t, 2H, J=7.2 Hz, thiol-compound-side methylene group adjacent to S), 2.70 (dd, 1H, J=5.4, 13.5 Hz, polyether-compound-side methylene group adjacent to S), 2.64 (t, 2H, J=7.2 Hz, methylene hydrogens at α position of ester carbonyl group), 2.62 (dd, 1H, J=7.5, 13.5 Hz, polyether-compound-side methylene group adjacent to S), 2.34 (br, 1H, OH).

Synthesis Example 5

Thioether-Containing Organic Compound (A-2)

3-(3-(methoxy(polyethoxy)ethoxy)-2-hydroxypropylsulfanyl) propionic acid (saponified addition compound in which methyl 3-mercaptopropionate is added to polyethylene glycol methyl glycidyl ether (molecular weight of polyethylene glycol chain: 2000))

[Chem. 6]

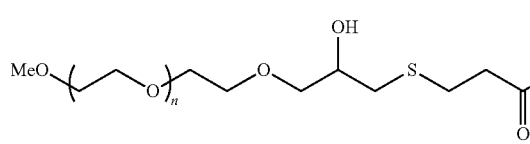

The thioether-containing organic compound (A-1) (1.162 g) obtained in Synthesis example 4 was dissolved in 3 mL of water. To this solution, a 0.273 mmol/mL aqueous solution of sodium hydroxide (2.2 mL, 0.6 mmol) was added and stirred at room temperature for an hour. This solution was adjusted to pH 1 with 1 mol/L nitric acid. To this solution, sodium sulfate was added, resulting in precipitation of oily matter. This oily matter was extracted with methylene chloride (15 mL, twice). The methylene chloride layer was collected, dried over anhydrous sodium sulfate, and then concentrated to dryness to provide 1.113 g of the target thioether-containing organic compound (A-2) (yield: about 96%).

$^1$H-NMR (deuterochloroform): δ=12.0 (br, 1H, —CO$_2$H), 3.9-3.4 (m, polyethylene glycol chain etc.), 3.38 (s, 3H, methoxy group at the terminal of PEG), 2.84 (t, 2H, J=7.2 Hz, thiol-compound-side methylene group adjacent to S), 2.70 (dd, 1H, J=5.6, 14.0 Hz, polyether-compound-side methylene group adjacent to S), 2.64 (dd, 1H, J=7.5, 14.0 Hz, polyether-compound-side methylene group adjacent to S), 2.63 (t, 2H, J=7.2 Hz, methylene hydrogens at α position of carboxylic group).

Synthesis Example 6

Thioether-Containing Organic Compound (A-3)

Ethyl 3-(methoxy(polyethoxy)ethoxy)-2-hydroxypropylsulfanyl acetate (addition compound in which ethyl mercaptoacetate is added to polyethylene glycol methyl glycidyl ether (molecular weight of polyethylene glycol chain: 2000))

[Chem. 7]

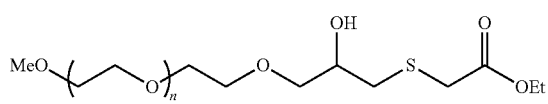

Synthesis was performed as in Synthesis example 4 except that ethyl mercaptoacetate (174 mg, 1.45 mmol) was used instead of methyl 3-mercaptopropionate (221 mg, 1.84 mmol) in Synthesis example 4. As a result, 1.04 g of the target thioether-containing organic compound (A-3) was provided (yield: about 98%).

$^1$H-NMR (deuterochloroform): δ=4.19 (q, 2H, J=6.9 Hz, hydrogens of methylene adjacent to O of ethyl ester), 3.9-3.4 (m, polyethylene glycol chain etc.), 3.38 (s, 3H, methoxy group at the terminal of PEG), 3.30 (s, 2H, —SCH$_2$CO—), 2.82 (dd, 1H, J=5.1, 13.8 Hz, polyether-compound-side methylene group adjacent to S), 2.64 (dd, 1H, J=7.5, 13.8 Hz, polyether-compound-side methylene group adjacent to S), 2.58 (br, 1H, OH), 1.29 (t, 3H, J=6.9 Hz, methyl hydrogens of ethyl ester).

Synthesis Example 7

Thioether-containing organic compound (A-4)

3-(methoxy(polyethoxy)ethoxy)-2-hydroxypropylsulfanyl acetic acid (saponified addition compound in which ethyl mercaptoacetate is added to polyethylene glycol methyl glycidyl ether (molecular weight of polyethylene glycol chain: 2000))

[Chem. 8]

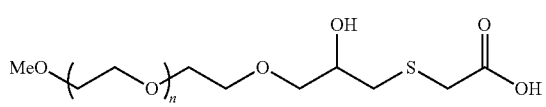

The thioether-containing organic compound (A-3) (1.00 g) obtained in Synthesis example 6 was dissolved in 3 mL of water. To this solution, a 0.273 mmol/mL aqueous solution of sodium hydroxide (2.2 mL, 0.6 mmol) was added and stirred at room temperature for an hour. This solution was adjusted to pH 1 with 1 mol/L nitric acid. To this solution, sodium sulfate was added, resulting in precipitation of oily matter. This oily matter was extracted with methylene chloride (15 mL, twice). The methylene chloride layer was collected, dried over anhydrous sodium sulfate, and then concentrated to dryness to provide 0.93 g of the target thioether-containing organic compound (A-4) (yield: about 94%).

$^1$H-NMR (deuterochloroform): δ=12.3 (br, 1H, —CO$_2$H), 3.9-3.4 (m, polyethylene glycol chain etc.), 3.38 (s, 3H, methoxy group at the terminal of PEG), 3.33 (s, 2H, —SCH$_2$CO—), 2.82 (dd, 1H, J=4.8, 14.1 Hz, polyether-compound-side methylene group adjacent to S), 2.64 (dd, 1H, J=6.9, 14.1 Hz, polyether-compound-side methylene group adjacent to S).

Synthesis Example 8

Thioether-Containing Organic Compound (A-5)

Ethyl 2-(3-(methoxy(polyethoxy)ethoxy)-2-hydroxypropylsulfanyl)propionate (addition compound in which ethyl 2-mercaptopropionate is added to polyethylene glycol methyl glycidyl ether (molecular weight of polyethylene glycol chain: 2000))

[Chem. 9]

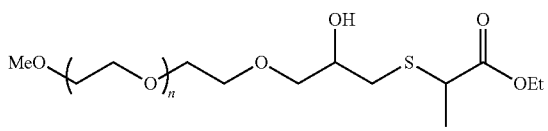

Synthesis was performed as in Synthesis example 4 except that ethyl 2-mercaptopropionate (247 mg, 1.84 mmol) was used instead of methyl 3-mercaptopropionate (221 mg, 1.84 mmol) in Synthesis example 4. As a result, 1.01 g of the thioether-containing organic compound (A-5) was provided (yield: about 95%).

$^1$H-NMR (deuterochloroform): δ=4.19 (q, 2H, J=6.9 Hz, hydrogens of methylene adjacent to O of ethyl ester), 3.9-3.5 (m, polyethylene glycol chain etc.), 3.38 (s, 3H, methoxy group at the terminal of PEG), 2.9-2.6 (dd (four lines), 2H, polyether-compound-side methylene group adjacent to S, syn/anti isomer mixture), 1.9 (br, 1H, OH), 1.45 (d, 3H, J=7.2 Hz, β-position methyl group of carboxylic group), 1.29 (t, 3H, J=6.9 Hz, methyl hydrogens of ethyl ester).

Synthesis Example 9

Thioether-containing organic compound (A-6)

2-(3-(methoxy(polyethoxy)ethoxy)-2-hydroxypropylsulfanyl) propionic acid (saponified addition compound in which ethyl 2-mercaptopropionate is added to polyethylene glycol methyl glycidyl ether (molecular weight of polyethylene glycol chain: 2000))

[Chem. 10]

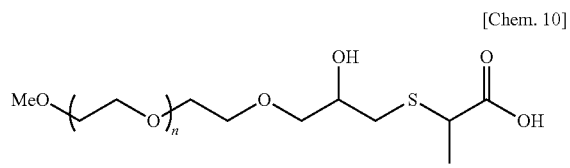

The thioether-containing organic compound (A-5) (1.00 g) obtained in Synthesis example 8 was dissolved in 3 mL of water. To this solution, a 0.273 mmol/mL aqueous solution of sodium hydroxide (2.2 mL, 0.6 mmol) was added and stirred at room temperature for an hour. This solution was adjusted to pH 1 with 1 mol/L nitric acid. To this solution, sodium sulfate was added, resulting in precipitation of oily matter. This oily matter was extracted with methylene chloride (15 mL, twice). The methylene chloride layer was collected, dried over anhydrous sodium sulfate, and then concentrated to dryness to provide 0.89 g of the target thioether-containing organic compound (A-6) (yield: about 90%).

$^1$H-NMR (deuterochloroform): δ=3.9-3.5 (m, polyethylene glycol chain etc.), 3.38 (s, 3H, methoxy group at the terminal of PEG), 2.93, 2.86, 2.80, 2.72 (dd (four lines), 2H, J=4.8, 14.1 Hz, J=6.6, 14.1 Hz, 5.7, 14.1 Hz, 7.5, 14.1 Hz, polyether-compound-side methylene group adjacent to S, syn/anti isomer), 1.44 (d, 3H, J=7.2 Hz, β-position methyl group of carboxylic group).

Synthesis Example 10

Thioether-containing organic compound (A-7)

3-(methoxy(polyethoxy)ethoxy)-1-(2-hydroxyethylsulfanyl)-2-propanol (addition compound in which thioglycol is added to polyethylene glycol methyl glycidyl ether (molecular weight of polyethylene glycol chain: 2000))

[Chem. 11]

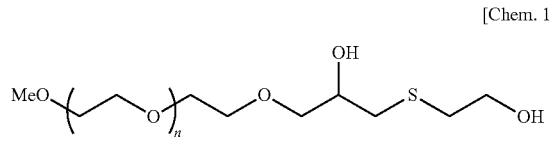

Synthesis was performed as in Synthesis example 4 except that thioglycol (113 mg, 1.45 mmol) was used instead of methyl 3-mercaptopropionate (221 mg, 1.84 mmol) in Synthesis example 4. As a result, 1.03 g of the target thioether-containing organic compound (A-7) was provided (yield: about 99%).

$^1$H-NMR (deuterochloroform): δ=3.8-3.4 (m, polyethylene glycol chain etc.), 3.74 (t, 2H, J=5.7 Hz, thiol-compound-side methylene group adjacent to O), 3.38 (s, 3H, methoxy group at the terminal of PEG), 2.88 (br, 2H, OH), 2.76 (t, 2H, J=5.7 Hz, thiol-compound-side methylene group adjacent to S), 2.72 (dd, 1H, J=5.4, 13.5 Hz, one of hydrogens of polyether-compound-side methylene adjacent to S), 2.64 (dd, 1H, J=6.9, 13.5 Hz, one of hydrogens of polyether-compound-side methylene adjacent to S).

Synthesis Example 11

Thioether-containing organic compound (A-8)

n-butyl 3-(3-(methoxy(polyethoxy)ethoxy)-2-hydroxypropylsulfanyl)propionate (addition compound in which butyl 3-mercaptopropionate is added to polyethylene glycol methyl glycidyl ether (molecular weight of polyethylene glycol chain: 2000))

[Chem. 12]

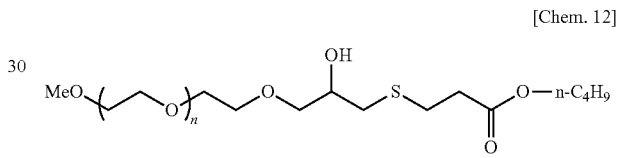

Synthesis was performed as in Synthesis example 4 except that butyl 3-mercaptopropionate (243 mg, 1.50 mmol) was used instead of methyl 3-mercaptopropionate (221 mg, 1.84 mmol) in Synthesis example 4. As a result, 0.651 g of the target thioether-containing organic compound (A-8) was provided (yield: about 58%).

$^1$H-NMR (deuterochloroform): δ=4.10 (t, 2H, methylene group adjacent to O in butyl ester), 3.9-3.4 (m, polyethylene glycol chain etc.), 3.38 (s, 3H, methoxy group at the terminal of PEG), 2.83 (t, 2H, J=7.2 Hz, thiol-compound-side methylene group adjacent to S), 2.71 (dd, 1H, J=5.7, 13.5 Hz, one of hydrogens of polyether-compound-side methylene adjacent to S), 2.62 (t, 2H, J=7.2 Hz, methylene hydrogens at α position of carboxylic group), 2.62 (dd, 1H, J=7.2, 13.5 Hz, one of hydrogens of polyether-compound-side methylene adjacent to S), 2.48 (br, 1H, OH), 1.63 (m, 2H, butyl ester methylene group), 1.37 (m, 2H, butyl ester methylene group), 0.94 (t, 3H, J=7.4 Hz, methyl group at the terminal of butyl ester).

Synthesis Example 12

Thioether-containing organic compound (A-9)

3-(methoxy(polyethoxy)ethoxy)-1-(n-octylsulfanyl)-2-propanol (addition compound in which 1-octanethiol is added to polyethylene glycol methyl glycidyl ether (molecular weight of polyethylene glycol chain: 2000)

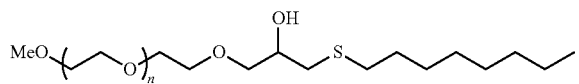

Synthesis was performed as in Synthesis example 4 except that 1-octanethiol (212 mg, 1.45 mmol) was used instead of methyl 3-mercaptopropionate (221 mg, 1.84 mmol) in Synthesis example 4. As a result, 0.338 g of the target thioether-containing organic compound (A-9) was provided (yield: about 32%).

$^1$H-NMR (deuterochloroform): δ=3.9-3.4 (m, polyethylene glycol chain etc.), 3.38 (s, 3H, methoxy group at the terminal of PEG), 2.66 (dd, 1H, J=5.7, 13.5 Hz, one of hydrogens of polyether-compound-side methylene adjacent to S), 2.61 (dd, 1H, J=7.2, 13.5 Hz, one of hydrogens of polyether-compound-side methylene adjacent to S), 2.54 (t, 2H, J=7.5 Hz, —S—CH$_2$ (octyl group)), 2.46 (br, 1H, OH), 1.6-1.2 (m, 12H, —CH$_2$— (octyl group)), 0.88 (t, 3H, J=6.9 Hz, —CH$_3$ (octyl group)).

Synthesis example 13

Thioether-containing organic compound (A-10)

3-(methoxy(polyethoxy)ethoxy)-1-phenylsulfanyl-2-propanol (addition compound in which benzenethiol is added to polyethylene glycol methyl glycidyl ether (molecular weight of polyethylene glycol chain: 2000))

[Chem. 14]

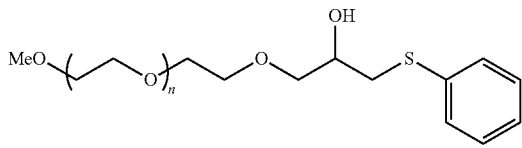

Synthesis was performed as in Synthesis example 4 except that benzenethiol (159 mg, 1.45 mmol) was used instead of methyl 3-mercaptopropionate (221 mg, 1.84 mmol) in Synthesis example 4. As a result, 0.974 g of the target thioether-containing organic compound (A-10) was provided (yield: about 93%).

$^1$H-NMR (deuterochloroform): δ=7.4-7.1 (m, 5H, Ph-H), 3.9-3.4 (m, polyethylene glycol chain etc.), 3.38 (s, 3H, methoxy group at the terminal of PEG), 3.27 (br, 1H, OH), 3.08 (dd, 1H, J=6.3, 13.5 Hz, one of hydrogens of polyether-compound-side methylene adjacent to S), 3.05 (dd, 1H, J=6.8, 13.5 Hz, one of hydrogens of polyether-compound-side methylene adjacent to S).

Synthesis Example 14

Thioether-containing organic compound (A-11)

3-(methoxy(polyethoxy)ethoxy)-1-(4-methoxyphenylsulfanyl-2-propanol (addition compound in which 4-methoxybenzenethiol is added to polyethylene glycol methyl glycidyl ether (molecular weight of polyethylene glycol chain: 2000))

[Chem. 15]

Synthesis was performed as in Synthesis example 4 except that 4-methoxybenzenethiol (203 mg, 1.45 mmol) was used instead of methyl 3-mercaptopropionate (221 mg, 1.84 mmol) in Synthesis example 4. As a result, 0.989 g of the target thioether-containing organic compound (A-11) was provided (yield: about 93%).

$^1$H-NMR (deuterochloroform): δ=7.37 (d, 2H, J=8.9 Hz, Ph-H (adjacent to S)), 6.84 (d, 2H, J=8.9 Hz, Ph-H (adjacent to O)), 3.9-3.4 (m, polyethylene glycol chain etc.), 3.79 (s, 3H, PhOCH$_3$), 3.38 (s, 3H, methoxy group at the terminal of PEG), 2.98 (dd, 1H, J=6.9, 13.5 Hz, one of hydrogens of polyether-compound-side methylene adjacent to S), 2.92 (dd, 1H, J=6.6, 13.5 Hz, one of hydrogens of polyether-compound-side methylene adjacent to S), 2.33 (br, 1H, OH).

Synthesis Example 15

Thioether-containing organic compound (A-12)

Ethyl 2-(3-(n-butoxy-poly(1-methylethoxy)-1-methylethoxy)-2-hydroxypropylsulfanyl)propionate (addition compound in which ethyl 2-mercaptopropionate is added to polypropylene glycol butyl glycidyl ether (molecular weight of polypropylene glycol chain: 2000))

[Chem. 16]

To the polypropylene glycol butyl glycidyl ether (molecular weight of polypropylene glycol chain: 2000, 2.00 g) obtained in Synthesis example 3, ethyl 2-mercaptopropionate (404 mg, 3.01 mmol) and 1 mol/L tetrabutylammonium fluoride/tetrahydrofuran solution (100 μL, 0.10 mmol) were added, then heated, and stirred at 70° C. to 75° C. for an hour. After the mixture was cooled, to this mixture, water (20 mL) and ethyl acetate (20 mL) were added, sufficiently stirred, and left to stand to achieve phase separation. After that, the ethyl acetate layer was washed with water (20 mL) twice. To the ethyl acetate layer, copper sulfate pentahydrate (about 1 g) was added and stirred for 10 minutes. The solid matter was filtered off and the filtrate was concentrated to provide the target thioether-containing organic compound (A-12) (2.33 g, yield: 97%).

$^1$H-NMR (deuterochloroform): δ=4.19 (q, 2H, J=6.9 Hz, methyl group adjacent to O in ethyl ester), 3.6-3.3 (m, polypropylene glycol chain, butyl-group methylene —OCH$_2$—, etc.), 2.8-2.6 (dd (four lines), 2H, one of hydrogens of polyether-compound-side methylene adjacent to S, syn/anti isomer mixture), 2.1 (br, 1H, OH), 1.44 (d, 3H, J=6.9 Hz, β-position methyl group of carboxylic group), 1.55 (m, 2H, methylene hydrogens in butyl group), 1.35 (m, 2H, methylene hydrogens in butyl group), 1.29 (t, 3H, J=6.9 Hz, ethylester methyl group), 1.14 (md, polypropylene methyl hydrogens), 0.91 (t, 3H, J=7.5 Hz, methyl hydrogens at the terminal of butyl group).

Synthesis Example 16

Polyethylene Glycol Methyl Glycidyl Ether (Molecular Weight of Polyethylene Glycol Chain: 400)

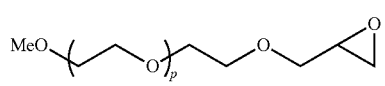

[Chem. 17]

Operations were performed as in Synthesis example 1 except that a polyethylene glycol monomethyl ether (molecular weight: 400, 100 g) was used instead of the polyethylene glycol monomethyl ether (molecular weight: 2000, 600 g) in Synthesis example 1. As a result, 104.2 g of the target compound was provided as an oily compound (yield: 72%).

$^1$H-NMR (deuterochloroform): δ=3.9-3.4 (m, polyethylene glycol chain etc.), 3.4 (m, 1H, one of hydrogens of methylene adjacent to oxirane ring), 3.38 (s, 3H, methoxy group at the terminal of PEG), 3.17 (m, 1H, methine hydrogen of oxirane ring), 2.79 (dd, 1H, J=4.2, 5.1 Hz, methylene hydrogen at the terminal of oxirane ring), 2.61 (dd, 1H, J=2.4, 5.1 Hz, 1H, methylene hydrogen at the terminal of oxirane ring).

Synthesis Example 17

Thioether-Containing Organic Compound (A-13)

Methyl 3-(3-(methoxy(polyethoxy)ethoxy)-2-hydroxypropylsulfanyl)propionate (addition compound in which methyl 3-mercaptopropionate is added to polyethylene glycol methyl glycidyl ether (molecular weight of polyethylene glycol chain: 1000))

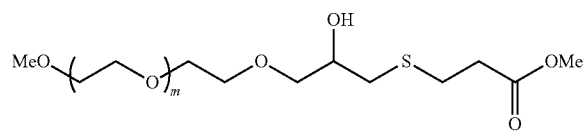

[Chem. 18]

To the polyethylene glycol methyl glycidyl ether (molecular weight of methoxy polyethylene glycol: 1000, 10.6 g) obtained in Synthesis example 2, methyl 3-mercaptopropionate (2.68 g, 20 mmol) and 1 mol/L tetrabutylammonium fluoride/tetrahydrofuran solution (500 μL, 0.5 mmol) were added, then heated, and stirred at 70° C. to 75° C. for 5 hours. After the mixture was cooled, to this mixture, 200 mL of water and 200 mL of ethyl acetate were added, sufficiently stirred, and left to stand to achieve phase separation. After that, the aqueous layer was washed with ethyl acetate (200 mL) twice. Addition of sodium sulfate to the aqueous layer resulted in precipitation of oily matter. This oily matter was extracted with methylene chloride (200 mL, three times). The methylene chloride layer was collected, dried over anhydrous sodium sulfate, and then concentrated to provide 10.6 g of the target thioether-containing organic compound (A-13) as oily matter (yield: about 89%).

$^1$H-NMR (deuterochloroform): δ=3.9-3.4 (m, polyethylene glycol chain etc.), 3.65 (s, 3H, ester methyl group), 3.38 (s, 3H, methoxy group at the terminal of PEG), 2.84 (t, 2H, J=7.2 Hz, thiol-compound-side methylene group adjacent to S), 2.70 (dd, 1H, J=5.4, 14.1 Hz, polyether-compound-side methylene group adjacent to S), 2.63 (t, 2H, J=7.2 Hz, methylene hydrogens at α position of ester carbonyl group), 2.61 (dd, 1H, J=5.4, 14.1 Hz, polyether-compound-side methylene group adjacent to S), 2.50 (br, 1H, OH).

Synthesis Example 18

Thioether-Containing Organic Compound (A-14)

3-(3-(methoxy(polyethoxy)ethoxy)-2-hydroxypropylsulfanyl) propionic acid (saponified compound of addition compound (A-13) in which methyl 3-mercaptopropionate is added to polyethylene glycol methyl glycidyl ether (molecular weight of polyethylene glycol chain: 1000)

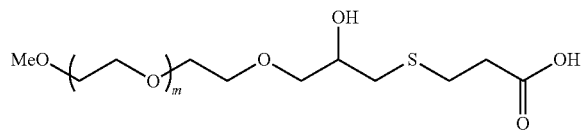

[Chem. 19]

The thioether-containing organic compound (A-13) (13.0 g) obtained in Synthesis example 17 was dissolved in 20 mL of water. To this solution, an aqueous solution prepared by dissolving sodium hydroxide (1.21 g) in water (10 mL) was added, and stirred at room temperature for an hour. This solution was adjusted to pH 1 with 1 mol/L nitric acid. To this solution, sodium sulfate was added, resulting in precipitation of oily matter. This oily matter was extracted with methylene chloride (150 mL and 50 mL). The methylene chloride layer was collected, dried over anhydrous sodium sulfate, and then concentrated to dryness to provide 11.5 g of the target thioether-containing organic compound (A-14) (yield: about 89%).

$^1$H-NMR (deuterochloroform): δ=3.9-3.4 (m, polyethylene glycol chain etc.), 3.38 (s, 3H, methoxy group at the terminal of PEG), 2.83 (t, 2H, J=6.9 Hz, thiol-compound-side methylene group adjacent to S), 2.73 (dd, 1H, J=5.4, 13.8 Hz, polyether-compound-side methylene group adjacent to S), 2.64 (dd, 1H, J=6.9, 13.8 Hz, polyether-compound-side methylene group adjacent to S), 2.64 (t, 2H, J=6.9 Hz, methylene hydrogens at α position of carboxylic group).

Synthesis Example 19

Thioether-Containing Organic Compound (A-15)

Methyl 3-(3-(methoxy(polyethoxy)ethoxy)-2-hydroxypropylsulfanyl)propionate (addition compound in which methyl 3-mercaptopropionate is added to polyethylene glycol methyl glycidyl ether (molecular weight of polyethylene glycol chain: 400))

[Chem. 20]

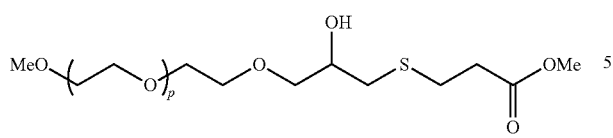

To the polyethylene glycol methyl glycidyl ether (molecular weight of methoxy polyethylene glycol: 400, 97.22 g) obtained in Synthesis example 16, methyl 3-mercaptopropionate (24.93 g, 20.75 mmol) and 1 mol/L tetrabutylammonium fluoride/tetrahydrofuran solution (10.4 mL, 10.4 mmol) were added, then heated, and stirred at 50° C. to 55° C. for 2 hours. After the mixture was cooled, to this mixture, 300 mL of water and 400 mL of ethyl acetate were added, sufficiently stirred, and left to stand to achieve phase separation. After that, the aqueous layer was washed with ethyl acetate (200 mL) twice. Addition of sodium sulfate to the aqueous layer resulted in precipitation of oily matter. This oily matter was extracted with methylene chloride (300 mL, three times). The methylene chloride layer was collected, dried over anhydrous sodium sulfate, and then concentrated to provide 115 g of the target thioether-containing organic compound (A-15) as oily matter (yield: about 94%).

$^1$H-NMR (deuterochloroform): δ=3.9-3.4 (m, polyethylene glycol chain etc.), 3.38 (s, 3H, methoxy group at the terminal of PEG), 2.84 (t, 2H, J=7.5 Hz, thiol-compound-side methylene group adjacent to S), 2.73 (dd, 1H, J=5.7, 13.8 Hz, polyether-compound-side methylene group adjacent to S), 2.64 (dd, 1H, J=6.9, 13.8 Hz, polyether-compound-side methylene group adjacent to S), 2.63 (t, 2H, J=7.5 Hz, methylene hydrogens at α position of carboxylic group).

Synthesis Example 20

Thioether-Containing Organic Compound (A-16)

Ethyl 3-ethoxycarbonylmethyl-3-(3-(methoxy(polyethoxy)ethoxy)-2-hydroxypropylsulfanyl)propionate (addition compound in which diethyl thiomalate is added to polyethylene glycol methyl glycidyl ether (molecular weight of polyethylene glycol chain: 2000))

[Chem. 21]

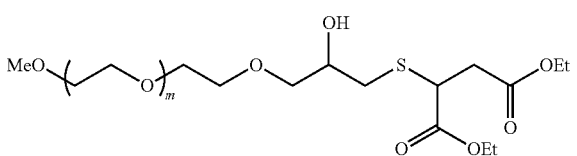

Synthesis was performed as in Synthesis example 4 except that diethyl thiomalate (199 mg, 0.96 mmol) was used instead of methyl 3-mercaptopropionate (221 mg, 1.84 mmol) in Synthesis example 4. As a result, 0.79 g of the target thioether-containing organic compound (A-16) was provided (yield: about 72%).

$^1$H-NMR (deuterochloroform): δ=4.4-4.1 (m, 4H, ester ethyl group, syn/anti isomer mixture), 3.9-3.4 (m, polyethylene glycol chain etc.), 3.38 and 3.39 (s, 3H, methoxy group at the terminal of PEG, syn/anti isomer mixture), 3.0-2.6 (m, 4H, thiol-compound-side and polyether-compound-side methylene group adjacent to S), 2.3 (br, 1H, OH), 1.3-1.2 (m, 6H, methyl hydrogens in ethyl ester groups, syn/anti isomer mixture).

Comparative Synthesis Example

Comparative Methacrylate Copolymer

To methyl ethyl ketone (hereafter MEK, 70 parts) being maintained at 80° C. under nitrogen flow and stirring, a mixture composed of 10 parts of methacrylic acid, 5 parts of benzyl methacrylate, 85 parts of methoxypolyethylene glycol methacrylate (molecular weight: 1000), 2 parts of thioglycolic acid, 80 parts of MEK, and 4 parts of a polymerization initiator ("PERBUTYL (registered trademark) O" [manufactured by NOF CORPORATION]) was added dropwise over 2 hours. After the dropping was completed, 2 parts of "PERBUTYL (registered trademark) O" was added and the solution was stirred at 80° C. for 22 hours. To the resultant reaction mixture, water was added; the solvent was evaporated under a reduced pressure and then the nonvolatile content was adjusted with water (nonvolatile content: 41%). The obtained copolymer had a weight-average molecular weight of 9800 (gel permeation chromatograph method) and an acid value of 76.5 mgKOH/g.

Example 1

Synthesis of Composite of Organic Compound and Copper Nanoparticles (Preparation of composite of organic compound and copper nanoparticles)

While nitrogen was blown at a flow rate of 50 mL/min into a mixture composed of copper(II) acetate monohydrate (3.00 g, 15.0 mmol), the thioether-containing organic compound (A-1) (0.451 g) obtained in Synthesis example 4 above, and ethylene glycol (10 mL), the mixture was heated, stirred at 125° C. for 2 hours with blowing, and deaerated. This mixture was allowed to cool to room temperature. To this mixture, a solution prepared by diluting hydrazine hydrate (1.50 g, 30.0 mmol) with 7 mL of water was slowly dropped with a syringe pump. At this time, generation of nitrogen due to the reduction reaction at the initial stage caused strong bubbling, which required caution. About a quarter of the amount was slowly dropped over 2 hours; at this time, the dropping was temporarily stopped and the solution was stirred for 2 hours until the bubbling ceased; and the remaining amount was further dropped over an hour. The resultant brown solution was heated to 60° C. and stirred for 2 hours to finish the reduction reaction. At this time, the red-brown reaction solution was sampled in a small amount over time, diluted with degassed purified water to which 0.1% hydrazine hydrate had been added, and immediately measured in terms of ultraviolet-visible absorption spectrum. As a result, a peak was observed in 570 to 580 nm. This peak was derived from plasmon resonance absorption caused by reduced copper having a size on the nanometer order. Thus, generation of copper nanoparticles was demonstrated (FIG. 1).

(Preparation of Aqueous Dispersion)

Figure 2:
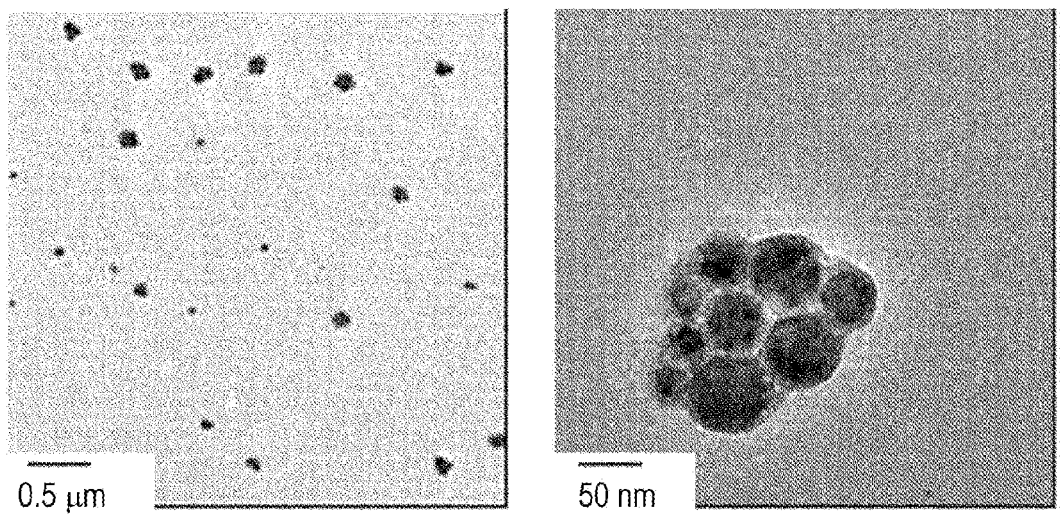
FIG. 2 illustrates transmission electron microscope images of copper nanoparticles in EXAMPLE 1.
Figure 3:
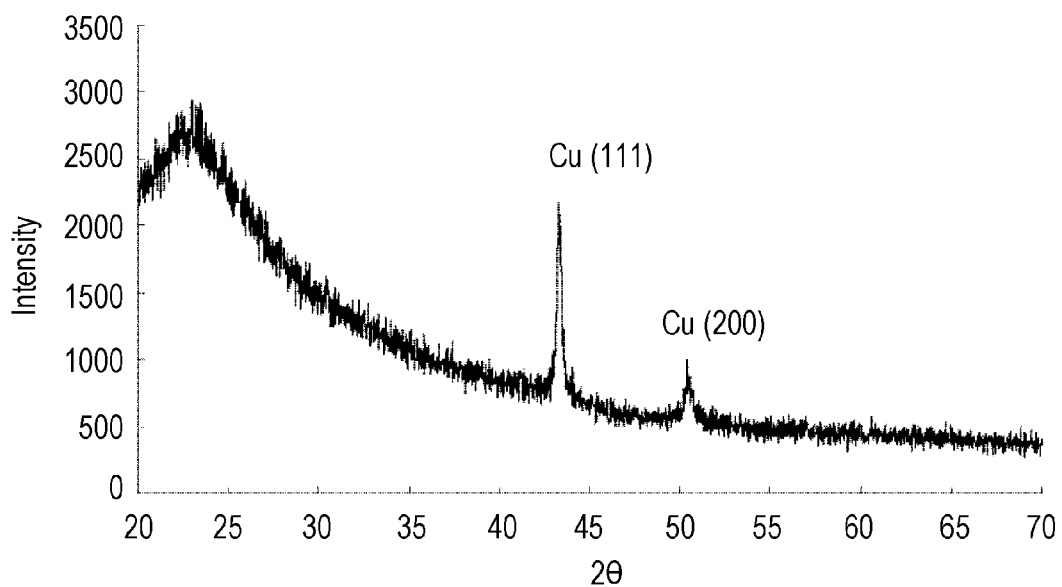
FIG. 3 illustrates a wide-angle X-ray diffraction spectrum of a dispersion of a composite of an organic compound and copper nanoparticles in EXAMPLE 1.

This reaction mixture was then circulated in a hollow-fiber ultrafiltration membrane module (HIT-1-FUS1582, 145 cm$^2$, cut-off molecular weight: 150,000) manufactured by Daicen Membrane Systems Ltd. While a 0.1% aqueous solution of hydrazine hydrate in the same amount as that of the filtrate discharged was added, the reaction mixture was purified through circulation until the filtrate from the ultrafiltration module reached the amount of about 500 mL. The supply of the 0.1% aqueous solution of hydrazine hydrate was stopped and the filtrate in that state was concentrated by the ultrafiltration process. Thus, an aqueous dispersion (2.85 g) of a composite of the organic compound and copper nanoparticles was obtained. The nonvolatile content of the dispersion was 16%. The metal content of the nonvolatile matter was 95%. Observation of the obtained copper particles with an electron microscope indicated that the copper particles were fine particles having a size of about 20 to about 60 nm (FIG. 2). The average particle size measured by dynamic light scattering at this time was 108 nm. From wide-angle X-ray diffractometry of the dispersion, it was demonstrated that the copper was reduced copper (FIG. 3).

Examples 2 to 14

Aqueous Dispersions of Composites of Organic Compounds and Copper Nanoparticles

Similarly, other thioether-containing organic compounds A-2 to 11 and A-13 to 16 were treated to prepare composites of organic compounds and copper nanoparticles. Portions of the reaction mixtures were sampled and measured in terms of ultraviolet-visible absorption spectrum. As a result, it was confirmed that, in all the cases where the compounds were used, absorption peaks derived from plasmon resonance in the surfaces of copper nanoparticles were observed in the range of 570 to 600 nm.

Example 15

A composite was prepared as in EXAMPLE 1 except that propylene glycol monomethyl ether acetate (10 mL) was used instead of ethylene glycol (10 mL) in EXAMPLE 1 and the thioether-containing organic compound A-12 was used as the protective agent. A portion of the reaction mixture was sampled and measured in terms of ultraviolet-visible absorption spectrum. As a result, it was confirmed that the absorption peak derived from plasmon resonance in the surfaces of copper nanoparticles was observed in the range of 570 to 600 nm.

Comparative Example 1

A reduction reaction was performed as in EXAMPLE 1 except that the Comparative methacrylate copolymer synthesized in Comparative synthesis example was used instead of the thioether-containing organic compound A-1 in EXAMPLE 1. As in EXAMPLE 1, a portion of the mixture after the reaction was sampled and measured in terms of ultraviolet-visible absorption spectrum. As a result, it was confirmed that no peak observed in the range of 570 to 600 nm was present.

Example 16

Synthesis of Composite of Organic Compound and Copper(I) Oxide Nanoparticles

Figure 9:
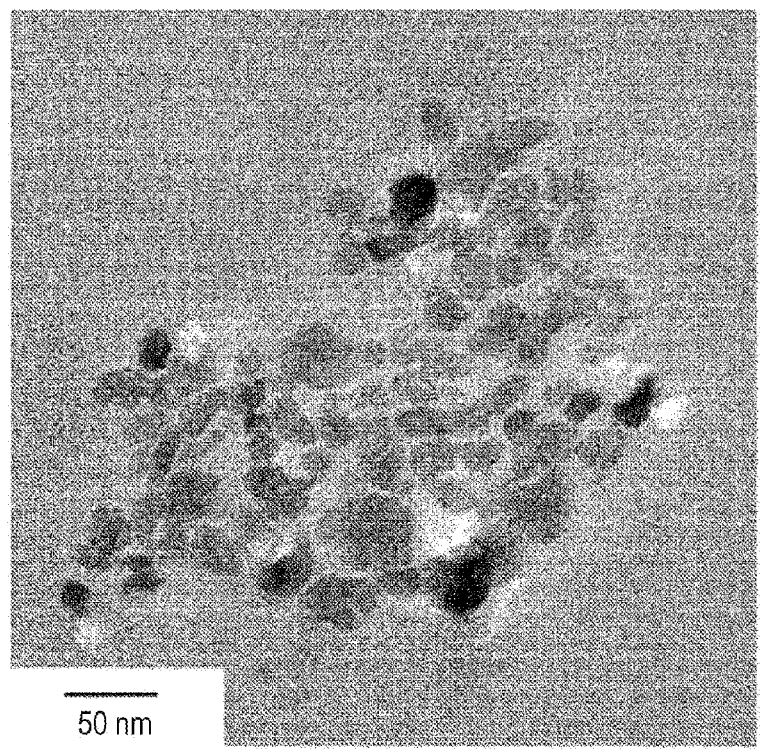
FIG. 9 illustrates a transmission electron microscope image of nano copper(I) oxide in EXAMPLE 16.
Figure 10:
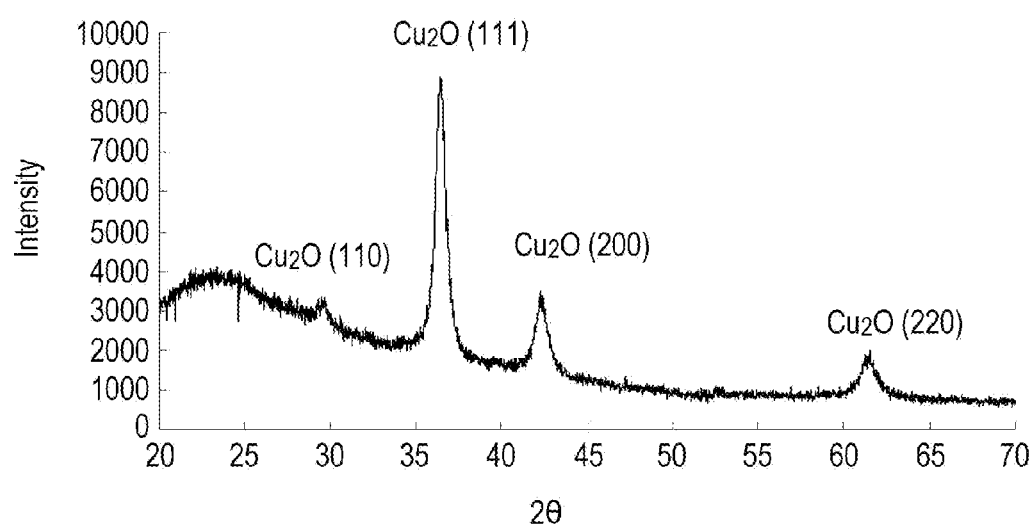
FIG. 10 illustrates a wide-angle X-ray diffraction spectrum of a dispersion liquid of a composite of an organic compound and copper(I) oxide nanoparticles in EXAMPLE 16.

While nitrogen was blown at a flow rate of 50 mL/min into a mixture composed of copper(II) acetate monohydrate (6.00 g, 30.1 mmol), the thioether-containing organic compound A-1 (0.902 g) obtained in Synthesis example 3 above, and ethylene glycol (20 mL), the mixture was heated and stirred at 125° C. for 2 hours with blowing. This mixture was allowed to cool to room temperature. To this mixture, a solution prepared by diluting N,N-diethylhydroxylamine (85%, 3.47 g, 33.1 mmol) with 14 mL of water was added. The solution was stirred at room temperature for 30 minutes, then transferred into a polyethylene centrifugation tube, subjected to an acceleration of 6000 G with a centrifuge for an hour to achieve centrifugal sedimentation. The supernatant liquor was discarded; to the sediment, water having been degassed by boiling for 30 minutes under nitrogen flow was added to disperse the sediment; this solution was subjected to centrifugation under the above-described conditions. This process was repeated twice. To the sediment, degassed water was added and the sediment was collected. Thus, 6.83 g of an aqueous dispersion liquid was obtained. The nonvolatile content was 21%. The content of nano copper(I) oxide in the nonvolatile matter was 95%. Observation of the sediment with an electron microscope revealed that the sediment was agglomerate of fine particles having a size of about 5 to about 20 nm (FIG. 9). From a wide-angle X-ray diffraction spectrum of the aqueous dispersion liquid, it was demonstrated that the generated product was copper(I) oxide ($Cu_2O$) (FIG. 10).

Application Example 1

Formation of Copper Thin Film and Resistivity Measurement of Thin Film

In a glove bag filled with argon, each of the aqueous dispersion liquids of composites obtained in EXAMPLES 1, 6, and 11 to 14 was dropped in an amount of about 0.1 mL at a position about 0.5 cm away from an end of a clean slide glass having dimensions of 7.6×1.3 cm, and spread with a bar coater (No. 16) to form a thin film. The thin film was dried in the same argon atmosphere. The thin film was then transferred into a glass container filled with argon and equipped with a thermometer. The atmosphere in the container was replaced with hydrogen by repeatedly performing pressure reduction with an aspirator and charging with hydrogen. The ambient temperature was increased to 180° C. with an oil bath and the heating was then performed for 2 hours. The container was then left to cool. The slide glass was taken out of the glass container and immediately measured in terms of electric resistivity. The results are described in Table 1.

TABLE 1

| | Thioether-containing organic compound | Resistivity of copper thin film (μΩcm) |
| --- | --- | --- |
| Example 1 | A-1 | 56 |
| Example 6 | A-6 | 9.8 |
| Example 11 | A-13 | 75 |
| Example 12 | A-14 | 78 |
| Example 13 | A-15 | 90 |
| Example 14 | A-16 | 56 |

Figure 4:
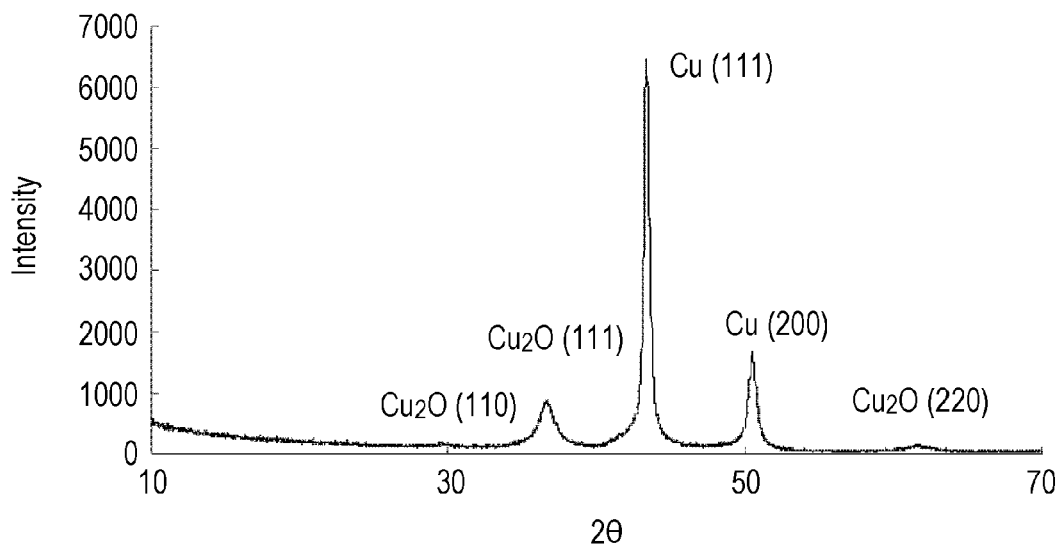
FIG. 4 illustrates a wide-angle X-ray diffraction spectrum of a sintered copper film in EXAMPLE 1.
Figure 5:
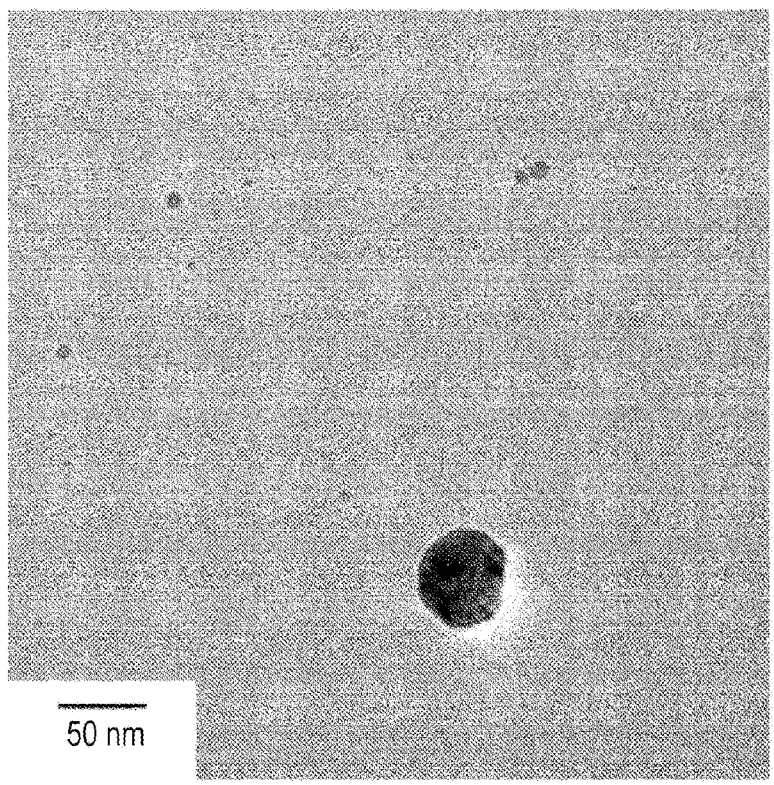
FIG. 5 illustrates a transmission electron microscope image of copper nanoparticles in EXAMPLE 2.
Figure 6:
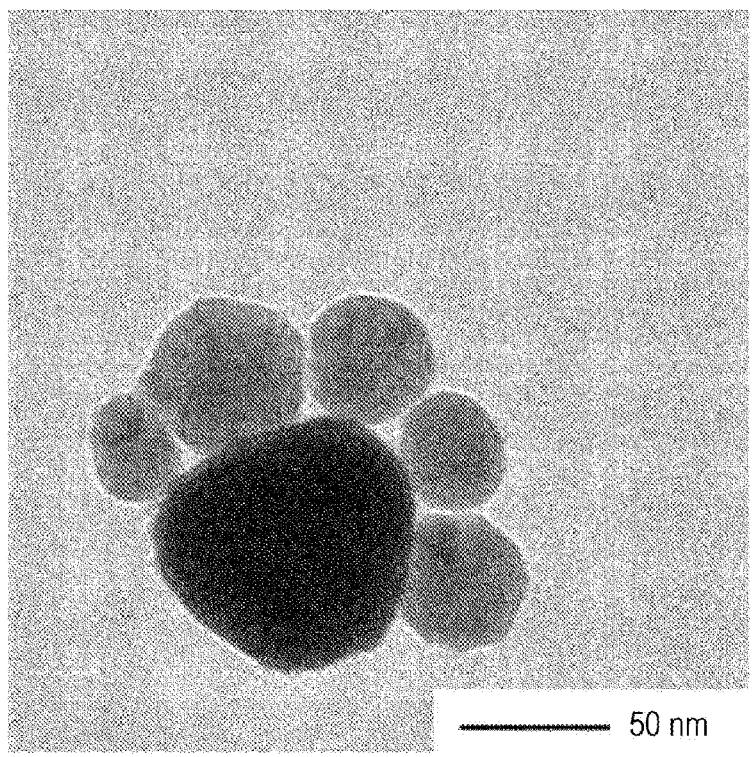
FIG. 6 illustrates a transmission electron microscope image of copper nanoparticles in EXAMPLE 11.
Figure 7:
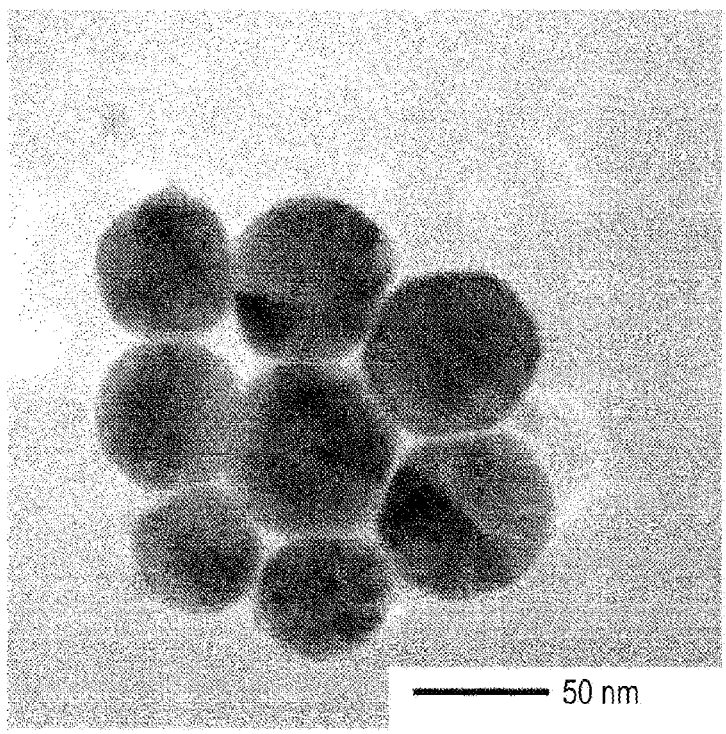
FIG. 7 illustrates a transmission electron microscope image of copper nanoparticles in EXAMPLE 12.
Figure 8:
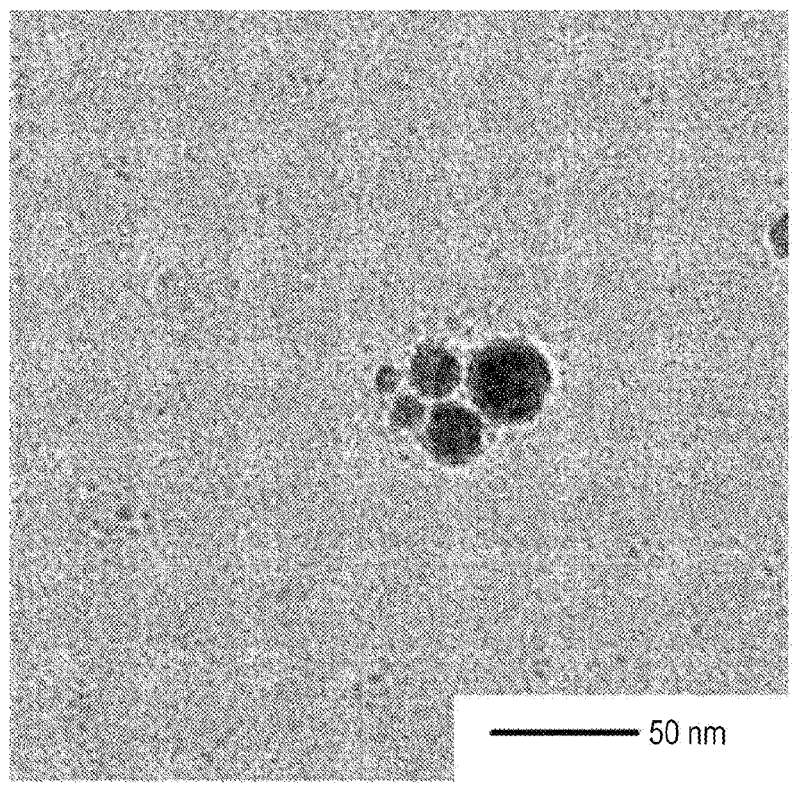
FIG. 8 illustrates a transmission electron microscope image of copper nanoparticles in EXAMPLE 13.

After the resistivity measurement was performed, the copper thin film formed from the dispersion in EXAMPLE 1 was subjected to wide-angle X-ray diffractometry. As a result, partial oxidation already proceeded and copper and a small amount of copper(II) oxide were detected (FIG. 4).

Application Example 2

Storage Stability of Aqueous Dispersions of Composites of Organic Compounds and Copper Nanoparticles The aqueous dispersion liquids of composites obtained in EXAMPLES 1, 6, and 11 to 14 were stored in polypropylene sealed vessels at room temperature and measured over time in terms of appearance and particle-size distribution by dynamic light scattering. As a result, the nano copper dispersions obtained in all the EXAMPLES did not change for 3 months (Table 2).

TABLE 2

| Appearance and average particle size ± standard deviation (nm) by dynamic light scattering | Immediately after production | 7 days elapsed | 1 month elapsed | 3 months elapsed |
|---|---|---|---|---|
| Example 1 | Dark red solution 108 ± 62 | Dark red solution 88 ± 23 | Dark red solution 103 ± 49 | Dark red solution 73 ± 18 |
| Example 6 | Dark red solution 78 ± 39 | Dark red solution 82 ± 28 | Dark red solution 80 ± 35 | Dark red solution 78 ± 30 |
| Example 11 | Dark red solution 88 ± 18 | Dark red solution 78 ± 35 | Dark red solution 82 ± 30 | Dark red solution 88 ± 25 |
| Example 12 | Dark red solution 62 ± 18 | Dark red solution 65 ± 21 | Dark red solution 68 ± 21 | Dark red solution 72 ± 25 |
| Example 13 | Deep dark red solution 35 ± 15 | Deep dark red solution 40 ± 18 | Deep dark red solution 39 ± 25 | Deep dark red solution 45 ± 22 |
| Example 14 | Dark red solution 108 ± 61 | Dark red solution 111 ± 078 | Dark red solution 105 ± 66 | Dark red solution 118 ± 43 |

Application Example 3

Storage Stability of Aqueous Dispersion of Composite of Organic Compound and Copper(I) Oxide Nanoparticles The aqueous dispersion of the composite obtained in EXAMPLE 16 was stored in a polypropylene sealed vessel at room temperature and measured over time in terms of appearance and particle-size distribution by dynamic light scattering. As a result, the aqueous dispersion did not change for a month (Table 3).

TABLE 3

| | Immediately after production | 7 days elapsed | 1 month elapsed |
|---|---|---|---|
| Appearance | Deep yellow solution | Deep yellow solution | Deep yellow solution |
| Average particle size ± standard deviation (nm) by dynamic light scattering | 111 ± 24 | 103 ± 48 | 86 ± 18 |

The invention claimed is:

1. A composite of an organic compound and copper nanoparticles, the composite comprising a thioether-containing organic compound (A) represented by a general formula (1) below and copper nanoparticles (B)

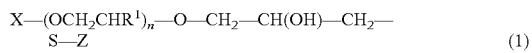 (1)

[in the formula (1), X represents a $C_1$ to $C_8$ alkyl group; $R^1$ represents a hydrogen atom or a methyl group; n represents a repeating number, an integer of 2 to 100; $R^1$ is independent between repeating units and may be the same or different; and Z represents a $C_2$ to $C_{12}$ alkyl group, an allyl group, an aryl group, an arylalkyl group, $-R^2-OH$, $-R^2-NHR^3$, or $-R^2-(COR^4)_m$ (where $R^2$ represents a $C_1$ to $C_4$ saturated hydrocarbon group; $R^3$ represents a hydrogen atom, a $C_2$ to $C_4$ acyl group, a $C_2$ to $C_4$ alkoxycarbonyl group, or a benzyloxycarbonyl group that may optionally have, as a substituent on the aromatic ring, a $C_1$ to $C_4$ alkyl group or a $C_1$ to $C_8$ alkoxy group; $R^4$ represents a hydroxy group, a $C_1$ to $C_4$ alkyl group, or a $C_1$ to $C_8$ alkoxy group; and m represents 1 to 3)].

2. The composite according to claim 1, wherein the thioether-containing organic compound (A) is prepared by a reaction between a polyether compound (a1) having a glycidyl group at an end and a thiol compound (a2).

3. The composite according to claim 1, wherein a content of the thioether-containing organic compound (A) in the composite is 2% to 8% by mass.

4. The composite according to claim 1, wherein the composite has a form of particles and, in the particles, an average particle size of 100 particles observed in a transmission electron microscope image is in a range of 2 to 80 nm.

5. A method for producing a composite of an organic compound and copper nanoparticles, the method comprising: in the presence of a thioether-containing organic compound (A) represented by a general formula (1) below

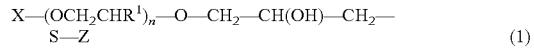 (1)

[in the formula (1), X represents a $C_1$ to $C_8$ alkyl group; $R^1$ represents a hydrogen atom or a methyl group; n represents a repeating number, an integer of 2 to 100; $R^1$ is independent between repeating units and may be the same or different; and Z represents a $C_2$ to $C_{12}$ alkyl group, an allyl group, an aryl group, an arylalkyl group, $-R^2-OH$, $-R^2-NHR^3$, or $-R^2-(COR^4)_m$ (where $R^2$ represents a $C_1$ to $C_4$ saturated hydrocarbon group; $R^3$ represents a hydrogen atom, a $C_2$ to $C_4$ acyl group, a $C_2$ to $C_4$ alkoxycarbonyl group, or a benzyloxycarbonyl group that may optionally have, as a substituent on the aromatic ring, a $C_1$ to $C_4$ alkyl group or a $C_1$ to $C_8$ alkoxy group; $R^4$ represents a hydroxy group, a $C_1$ to $C_4$ alkyl group, or a $C_1$ to $C_8$ alkoxy group; and m represents 1 to 3)]

(i) a step of mixing a divalent copper-ion compound with a solvent; and (ii) a step of reducing the copper ions to zero-valent copper nanoparticles (B).

6. The production method according to claim 5, wherein the thioether-containing organic compound (A) is prepared by a reaction between a polyether compound (a1) having a glycidyl group at an end and a thiol compound (a2).

7. The method for producing a composite according to claim 5, wherein a reduction reaction of the step (ii) is performed with a hydrazine hydrate, uns-dimethylhydrazine, an aqueous solution of hydroxylamine, or sodium borohydride.

8. The method for producing a composite according to claim 7, wherein a reduction reaction of the step (II') is performed with a hydrazine hydrate, uns-dimethylhydrazine, an aqueous solution of hydroxylamine, ascorbic acid, acetaldehyde, hydroxyacetone, or N,N-diethylhydroxylamine.

9. A composite of an organic compound and copper(I) oxide nanoparticles, the composite comprising a thioether-containing organic compound (A) represented by a general formula (1) below and copper(I) oxide nanoparticles (C)

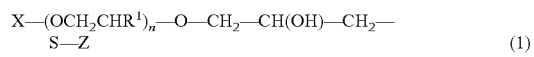 (1)

[in the formula (1), X represents a $C_1$ to $C_8$ alkyl group; $R^1$ represents a hydrogen atom or a methyl group; n represents a repeating number, an integer of 2 to 100; $R^1$ is independent between repeating units and may be the same or different; and Z represents a $C_2$ to $C_{12}$ alkyl group, an allyl group, an aryl group, an arylalkyl group, $-R^2-OH$, $-R^2-NHR^3$, or $-R^2-(COR^4)_m$ (where $R^2$ represents a $C_1$ to $C_4$ saturated hydrocarbon group; $R^3$ represents a hydrogen atom, a $C_2$ to $C_4$ acyl group, a $C_2$ to $C_4$ alkoxycarbonyl group, or a benzyloxycarbonyl group that may optionally have, as a substituent on the aromatic ring, a $C_1$ to $C_4$ alkyl group or a $C_1$ to $C_8$ alkoxy group; $R^4$ represents a hydroxy group, a $C_1$ to $C_4$ alkyl group, or a $C_1$ to $C_8$ alkoxy group; and m represents 1 to 3)].

10. The composite according to claim 9, wherein the thioether-containing organic compound (A) is prepared by a reaction between a polyether compound (a1) having a glycidyl group at an end and a thiol compound (a2).

11. The composite according to claim 9, wherein a content of the thioether-containing organic compound (A) in the composite is 2% to 8% by mass.

12. The composite according to claim 9, wherein the composite has a form of particles and, in the particles, an average particle size of 100 particles observed in a transmission electron microscope image is in a range of 2 to 80 nm.

13. A method for producing a composite of an organic compound and copper(I) oxide nanoparticles, the method comprising: in the presence of a thioether-containing organic compound (A) represented by a general formula (1) below

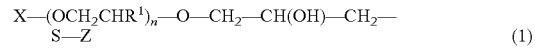

[in the formula (1), X represents a $C_1$ to $C_8$ alkyl group; $R^1$ represents a hydrogen atom or a methyl group; n represents a repeating number, an integer of 2 to 100; $R^1$ is independent between repeating units and may be the same or different; and Z represents a $C_2$ to $C_{12}$ alkyl group, an allyl group, an aryl group, an arylalkyl group, $-R^2-OH$, $-R^2-NHR^3$, or $-R^2-(COR^4)_m$ (where $R^2$ represents a $C_1$ to $C_4$ saturated hydrocarbon group; $R^3$ represents a hydrogen atom, a $C_2$ to $C_4$ acyl group, a $C_2$ to $C_4$ alkoxycarbonyl group, or a benzyloxycarbonyl group that may optionally have, as a substituent on the aromatic ring, a $C_1$ to $C_4$ alkyl group or a $C_1$ to $C_8$ alkoxy group; $R^4$ represents a hydroxy group, a $C_1$ to $C_4$ alkyl group, or a $C_1$ to $C_8$ alkoxy group; and m represents 1 to 3)]

(i) a step of mixing a divalent copper-ion compound with a solvent; and (ii') a step of reducing the copper ions to monovalent copper(I) oxide nanoparticles (C).

14. The production method according to claim 13, wherein the thioether-containing organic compound (A) is prepared by a reaction between a polyether compound (a1) having a glycidyl group at an end and a thiol compound (a2).

\* \* \* \* \*